US009782361B2

(12) United States Patent
De Witte et al.

(10) Patent No.: US 9,782,361 B2
(45) Date of Patent: Oct. 10, 2017

(54) ANTICONVULSANT ACTIVITY OF TURMERIC OIL AND BISABOLENE SESQUITERPENOIDS

(75) Inventors: Peter A. M. De Witte, Predikherenberg (BE); Camila V. Esguerra, Herent (BE); Alexander D. Crawford, Herent (BE); Adriana Monserrath Orellana Paucar, Cuenca (EC)

(73) Assignee: Katholieke Universiteit Leuven (BE)

( * ) Notice: Subject to any disclaimer, the term of this patent is extended or adjusted under 35 U.S.C. 154(b) by 0 days.

(21) Appl. No.: 14/130,702

(22) PCT Filed: Jul. 4, 2012

(86) PCT No.: PCT/EP2012/063027
§ 371 (c)(1),
(2), (4) Date: Jan. 3, 2014

(87) PCT Pub. No.: WO2013/004740
PCT Pub. Date: Jan. 10, 2013

(65) Prior Publication Data
US 2014/0243420 A1 Aug. 28, 2014

(30) Foreign Application Priority Data
Jul. 4, 2011 (GB) .................................... 1111319.8

(51) Int. Cl.
*A61K 31/12* (2006.01)
*A61K 31/121* (2006.01)
*A61K 36/9066* (2006.01)

(52) U.S. Cl.
CPC ............ *A61K 31/12* (2013.01); *A61K 31/121* (2013.01); *A61K 36/9066* (2013.01)

(58) Field of Classification Search
CPC .................................................... A61K 31/12
See application file for complete search history.

(56) References Cited

U.S. PATENT DOCUMENTS

2006/0003989 A1* 1/2006 Quay .................. A61K 9/0043
514/214.03

FOREIGN PATENT DOCUMENTS

| CN | 101199833 A | 6/2008 |
|---|---|---|
| WO | 03051380 A2 | 6/2003 |
| WO | 2007109210 A2 | 9/2007 |
| WO | 2010045577 A2 | 4/2010 |
| WO | 2011014880 A1 | 2/2011 |
| WO | 2011080090 A1 | 7/2011 |
| WO | 2011114350 A2 | 9/2011 |
| WO | 2011125070 A2 | 10/2011 |

OTHER PUBLICATIONS

Ahmed et al., "Inhibitory effect of curcuminoids on acetylcholinesterase activity and attenuation of scopolamine-induced amnesia may explain medicinal use of turmeric in Alzheimer's disease", Pharmacology Biochemistry and Behavior, vol. 91, pp. 554-559, 2009.

Crawford et al., "Fishing for Drugs from Nature: Zebrafish as a Technology Platform for Natural Product Discovery", Planta Med. vol. 74, pp. 624-632, 2008.
Fujiwara et al., "Acetylcholinesterase Inhibitory Activity of Volatile Oil from Peltophorum dasyrachis Kurz ex Bakar (Hellow Batai) and Bisabolane-Type Sesquiterpenoids", Journal of Agricultural and Food Chemistry, vol. 58, No. 5, pp. 2824-2829, 2010.
Monserrath Orellana-Paucar et al., "Anticonvulsant activity of bisabolene sesquiterpenoids of Curcuma longa in zebrafish and mouse seizure models", Epilepsy and Behavior, vol. 24, No. 1, pp. 14-22, May 2012.
Park So-Young et al., "Discovery of Natural Products from Curcuma longa that Protect Cells from Beta-Amyloid Insult: A Drug Discovery Effort against Alzheimer's Disease", Journal of Natural Products, vol. 65, No. 9, Sep. 1, 2002.
Search Report and Written Opinion for International Application No. PCT/EP2012/063027 dated Aug. 29, 2012.
U.S. Federal Food and Drug Administration Safety Information—Regarding the use of Galantamine Hydrobromide, Reference ID 3699683, pp. 1-28, Revision date Feb. 2015.
Zimmer et al., Nerve Gas-Induced Seizures: Role of Acetylcholine in the Rapid Induction of Fos and Glial Fibrillary Acidic Protein in Piriform Cortex the Journal of Neuroscience 1998, 18(10): 3897-3908.
Kozhemyakin et al., Central Cholinesterase Inhibition Enhances Glutamatergic Synaptic Transmission J. Neurophysiol. 2010, 103: 1748-1757.
Peter G. Blain, Organophosphorous poisoning (acute) Clinical Evidence 2011, 05: 2102.
Todorovic et al., Characterization of status epilepticus induced by two organophosphates in rats Epilepsy Res. 2012, 101(3): 268-276.
World Health Organization. Atlas: Epilepsy Care in the World. s.l.: WHO Press, 2005. ISBN 9241563036.
Drug treatment of epilepsy: options and limitations. Schimdt, D. 2009, Epilepsy and Behavior, vol. 15, pp. 56-65.
Life-threatening adverse events of antiepileptic drugs. Arroyo, S. and de la Morena, A. 1-2, 2001, Epilepsy Res, vol. 47, pp. 155-174.
Complaints associated with the use of antiepileptic drugs: results from a community-based study. Carpaya, J., Aldenkampb, A. P. and van Donselaa, C. A. 3, 2005, Seizure, vol. 14, pp. 198-206.
Patient-reported cognitive side effects of antiepileptic drugs: Predictors and comparison of all commonly used antiepileptic drugs. Arifa, H., et al. 1, 2009, Epilepsy & Behaviour, vol. 14, pp. 202-209.
Cognitive and memory effects of the new antiepileptic drugs. Meador, K. 2006, Epilepsy Res, vol. 68, pp. 63-67.
Review on phytotherapy in epilepsy. Nsour, W. M., CB-S., Lau and I. C. K., Wong. 2000, Seizure, vol. 9, pp. 96-107.
New anticonvulsant agents. Malawska, B. 2005, Current topic in medicinal chemisty, vol. 5, pp. 69-85.

(Continued)

*Primary Examiner* — Yong Chong
(74) *Attorney, Agent, or Firm* — Dinsmore & Shohl LLP

(57) ABSTRACT

The present invention relates to the anti-convulsant activity of turmeric oil and its volatile bisabolene sesquiterpenoids ar- turmerone, α-turmerone, β-turmerone (curlone) and α-atlantone, as an anticonvulsant agent for the treatment of epilepsy and/or as therapeutic agents for the treatment of disorders of the central nervous system, including tremor, pain, mood disorders (including depression, bipolar disorder, attention deficit-hyperactivity disorder, and schizophrenia), and neurodegenerative diseases.

9 Claims, 14 Drawing Sheets

(56) References Cited

OTHER PUBLICATIONS

Losigamone. Schwabe, W. and Willmore, L. J. 2001, Curr. Op. Invet. Drugs, vol. 2, pp. 1763-1766.
WHO monographs on selected medicinal plants. World Health Organization. s.l.: WHO Library Cataloguing in Publication Data, 1999, vol. 1, pp. 115-124. ISBN 924154517 8.
Curcumin protects against electrobehavioral progression of seizures in the iron-induced experimental model of epileptogenesis. Jyoti, A., Sethi, P. and Sharma, D. 2009, Epilepsy & Behavior, vol. 14, pp. 300-308.
Protective role of curcumin in maximal electroshock induced seizures, memory impairment and neurotransmitters in rat brain. Jithendra, C., Murthy, T. and Upadyay, L. 1, 2008, Journal of Pre-Clinical and Clinical Res, vol. 2, pp. 35-39.
Prevention of kainic acid-induced changes in nitric oxide level and neuronal cell damage in the rat hippocampus by manganese complexes of curcumin and diacetylcurcumin. Sumanot, Y., et al. 2006, Life Sci, vol. 78, pp. 1884-1891.
Protective effect of curcumin against seizures and cognitive impairment in a pentylenetetrazol-kindled epileptic rat model. Mehla, J., et al. 19-22, 2010, Life Sci, vol. 87, pp. 596-603.
Curcuma oil modulates the nitric oxide system response to cerebral ischemia/reperfusion injury. Dohare, P., Varma, S. and Ray, M. 2008, Nitric Oxide, vol. 19, pp. 1-11.
Neuroprotective efficacy and therapeutic window of curcuma oil: in rat embolic stroke model. Dohare, P., et al. 55, 2008, BCM Complement Ahern Med, vol. 8.
Curcuma oil: reduces early accumulation of oxidative product and is anti-apoptogenic in transient focal ischemia in rat brain. Rathore, P., et al. 2008, Neurochem Res, vol. 33, pp. 1672-1682.
Anticonvulsant activity of furanocoumarins and the essential oil obtained from the fruits of Heracleum crenatifolium. Tosun, F., et al. 3, 2008, Food Chemistry, vol. 107, pp. 990-993.
Phytochemical screening and anticonvulsant activity of Cymbopogon winterianus Jowitt (Poacea) leaf essential oil in rodents. Quintans-Junior, L. J., et al. 8, 2008, Phytomedicine, vol. 15, pp. 619-624.
Anticonvulsant activity of the leaf essential oil of Laurus nobilis against pentylenetetrazole-and maximal electroshock-induced seizures. Sayyah, M., Valizadeh, J. and Kamalinejad, M. 3, 2002, Phytomedicine, vol. 9, pp. 212-216.
Acute effects of alcohol on larval zebrafish: a genetic system for large-scale screening. Lockwood, B., et al. 2009, Pharmacology, Biochemistry and Behavior, vol. 77, pp. 647-654.
In vivo drug discovery in the zebrafish. Zon, L. and Peterson, R. 2005, Nature Reviews Drug Discovery, vol. 4, pp. 35-44.
Pentylenetetrazole-induced changes in zebrafish behavior, neural activity, and c-fos expression. Baraban, S. C., Taylor, M. R.: Castro, P. A. and Baier, H. 3, 2005, Neuroscience, vol. 131, pp. 759-768.
Zebrafish offer the potential for a primary screen to identify a wide variety of potential anticonvulsants. Berghmans, S., et al. 1, 2007, Epilepsy Res, vol. 75, pp. 18-28.
Validation of a larval zebrafish locomotor assay for assessing the seizure liability of early-stage development drugs. Winter, M. J., et al. 2008, Journal of Pharmacological and Toxicological Methods, vol. 57, pp. 178-187.
Liquid chromatography-electrospray mass spectrometric analysis of curcuminoids and sesquiterpenoids in turmeric (Curcuma longa). He, X-G., et al. 1998, Journal of Chromatography A, vol. 818, pp. 127-132.
Acute seizure tests in epilepsy research: electroshock-and chemical-induced convulsions in the mice. Giardina, W. J. and Gasior, M. 5.22.27, 2009, Curr. Protoc. Pharmacol, vol. 45.
Total synthesis of (R)-and (S)-turmerone and (7S,9R)-bisacumol by an efficient chemoenzymatic approach. Kamal, A., et al. 11, 2009, Tetrahedron: Asymmetry, vol. 20, pp. 1267-1271.
New bisabolane sesquiterpenoids from the rhizomes of Curcuma xanthorrhiza (Zingiberacea). Uehara, S., et al. 1989, Chem Pharm Bull, vol. 37, pp. 237-240.
Preparation of $\gamma,\delta$-unsaturated $\beta$-ketophosphonates from tertiary $\alpha$-allenic alcohols. The Synthesis of ($\pm$)-(E)-$\alpha$-Atlantone. Friesen, R. W. and Blouin, M. 1996, J. Org. Chem, vol. 61, pp. 7202-7206.
Curcumin has anticonvulsant activity on increasing current electroshock seizures in mice. Bharal, N., et al. 2008, Phytotherapy Res, vol. 22, pp. 1660-1664.
A pilot cross-over study to evaluate human oral bioavailability of BCM-95 CG (Biocurcumax), a novel bioenhanced preparation of curcumin. Antony, B., et al. 4, 2008, Indian J Pharm Sci, vol. 70, pp. 445-449.
Early human safety study of turmeric oil (Curcuma longa oil) administered orally in healthy volunteers. Joshi, J., et al. 2003, JAPI, vol. 51.
Toxicity prediction of compounds from turmeric (Curcuma longa L.). Balaji, S. and Chempakam, B. 2010, Food Chem Toxicol, vol. 48, pp. 2951-2959.
$\alpha$-Tocopherol protects against pentylenetrazol-and methylmalonate-induced convulsions. Pereira, M., et al. 1, 2005, Epilepsy Res, vol. 66, pp. 185-194.
Regional vulnerability to oxidative stress in a model of experimental epilepsy. Lores Arnaiz, S., et al. 12, Neurochemical Res, vol. 23, pp. 1477-1483.
Protective effect of curcumin against seizures and cognitive impairment in a pentylenetetrazol-kindled epileptic rat model. Mehla J, Reeta K. H, Gupta P, Gupta Y. s.l.: Life Sci, 2010, vol. 87, Issues 19-22, pp. 596-603.
El Jazouli M, Lage N, Masson S, Thuillier A. s.l.: Bull Soc Chim Fr, 1988, vol. 5, pp. 883-888.
Pharmacological characterization of the 6 Hz psychomotor seizure model of partial epilepsy. Barton M E, Klein B D, Wolf H H, White H S. Epilepsy Res. Dec. 2001; 47(3):217-227.
Acetylcholinesterase Inhibitory Activity of Volatile Oil from Peltophorum dasyrachis Kurz ex Bakar (Yellow Batai) and Bisabolane-Type Sesquiterpenoids. Fujiwara M, Yagi N, Miyazawa M. J. Agric Food Chem. 2010, 58: 2824-2829.
Cholinergic Dysfunction in Temporal Lobe Epilepsy. Friedman A, Beherens C, Heinemann U. Epilepsia 2007, 48 (Supp15): 126-130.

\* cited by examiner

Figure 1
(A)
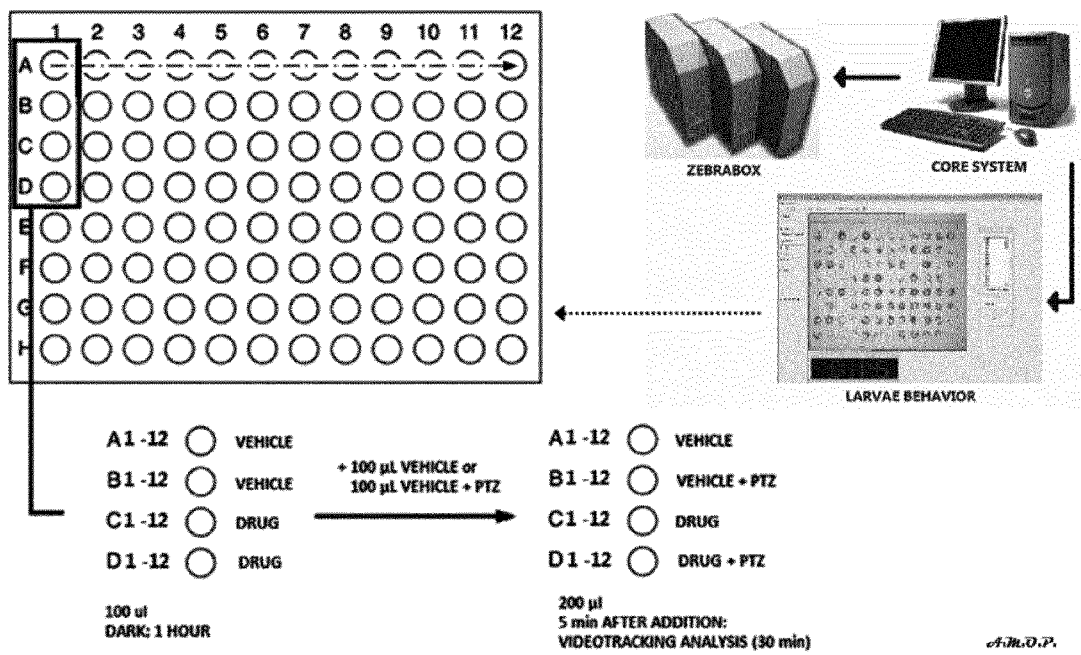
(B)
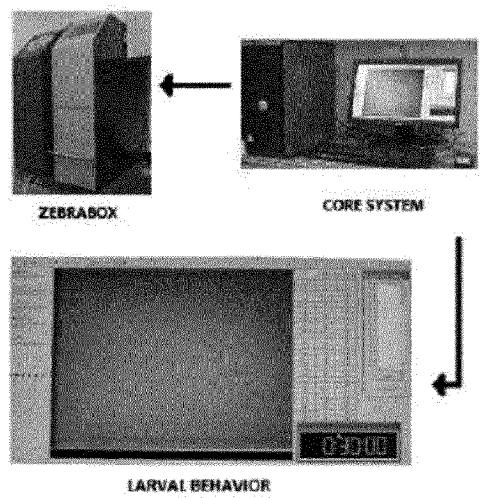

Figure 2.
A)
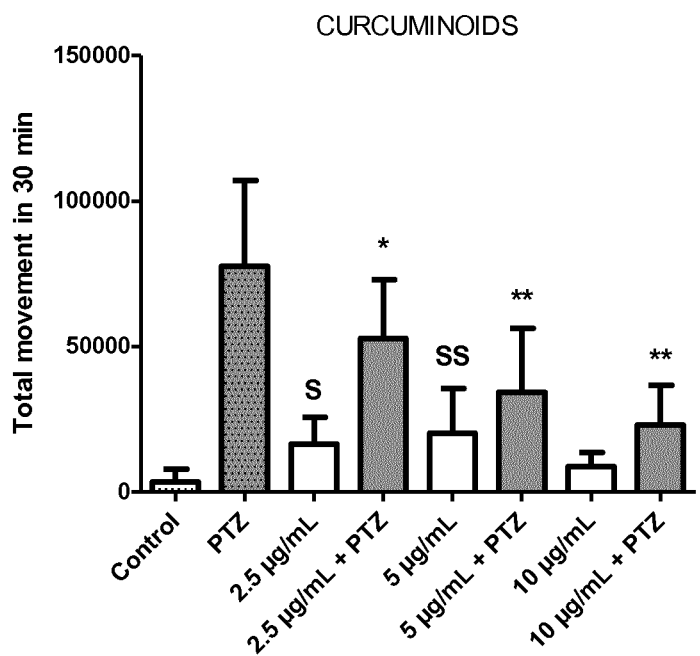
B)
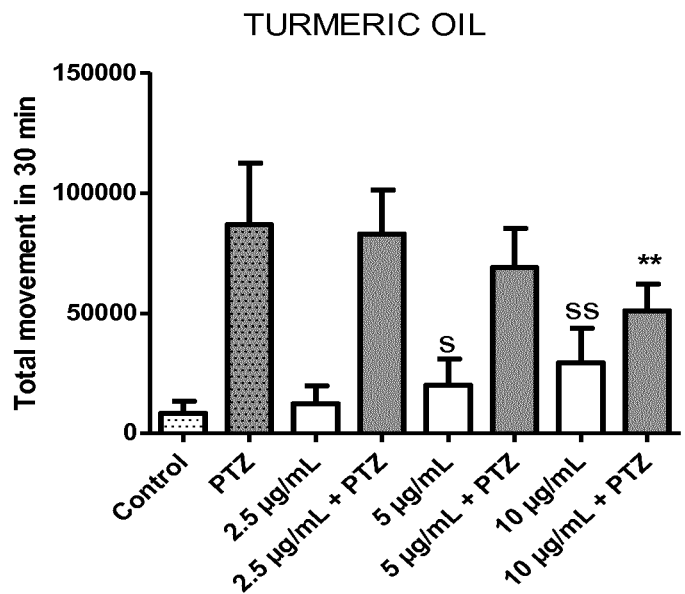

Figure 3
A)
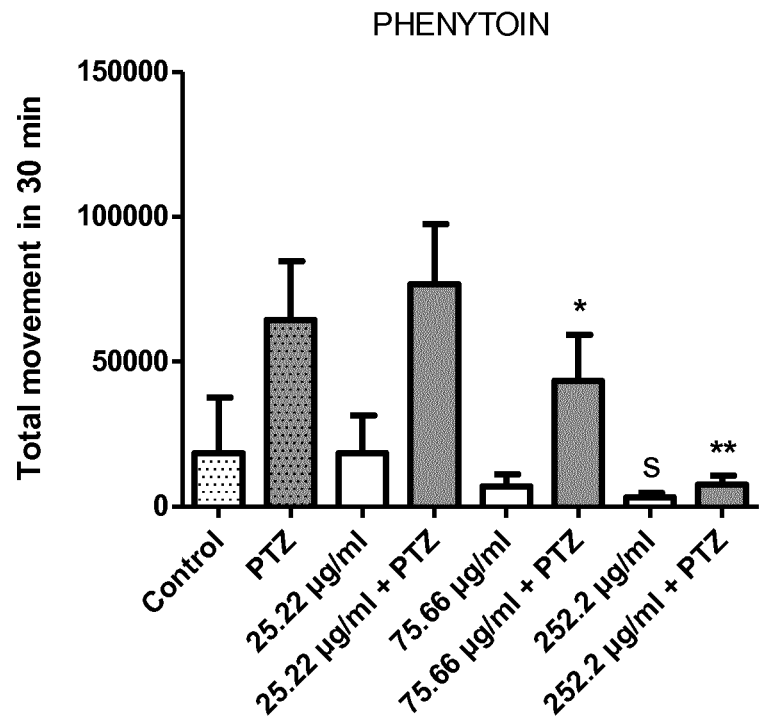
B)
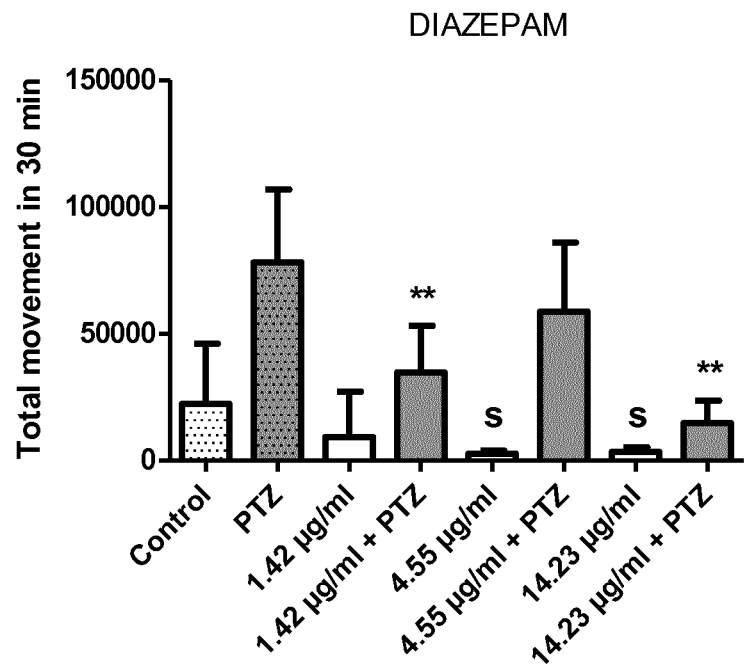

Figure 8
A)
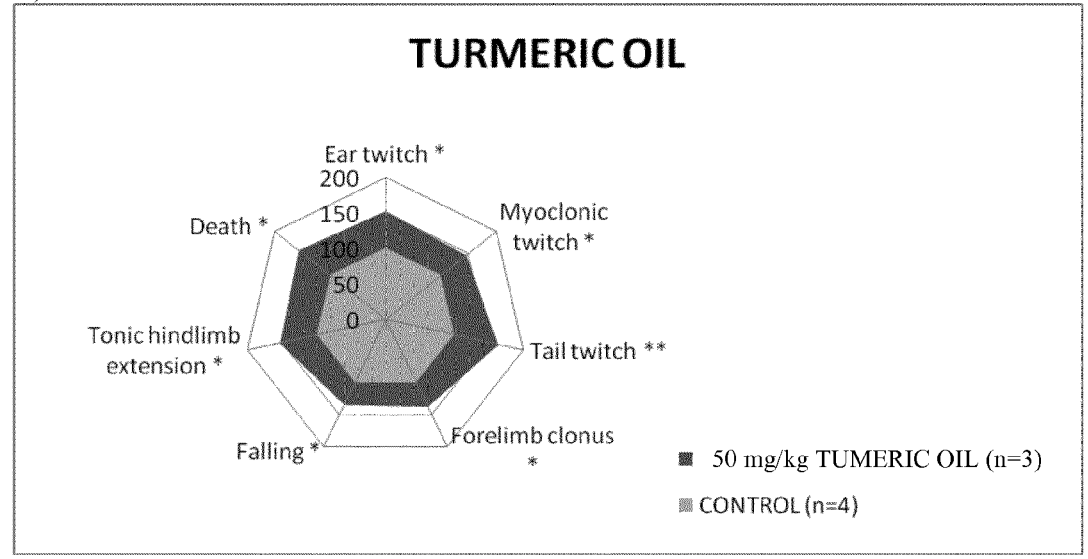
B)
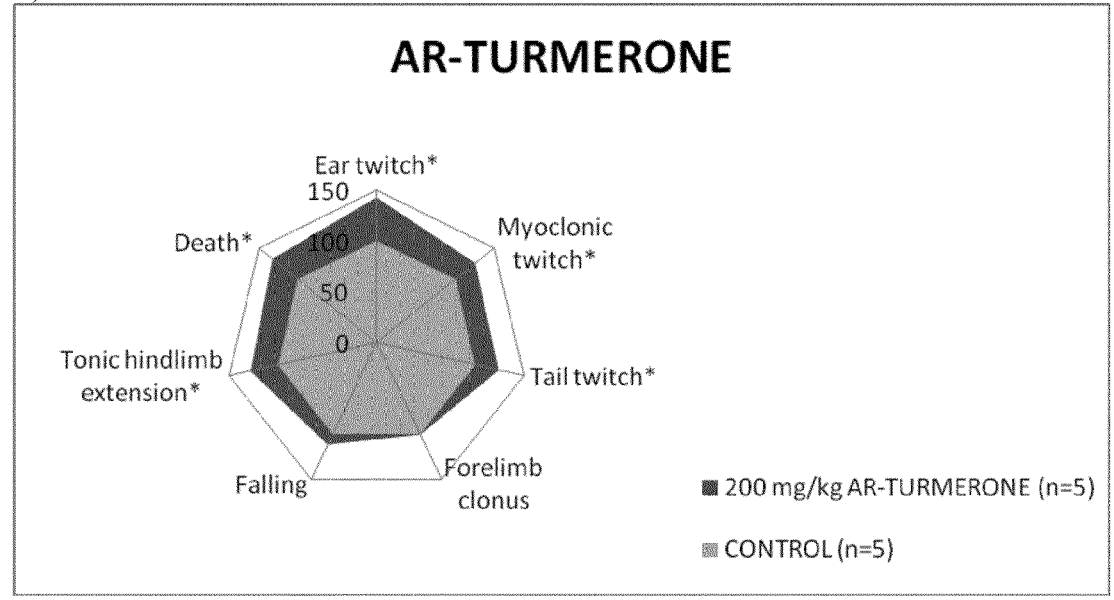

Figure 9
| Seizure parameters | PTZ dose required to elicit individual seizure parameters (mg/kg) | | |
|---|---|---|---|
| | Control (vehicle) n=5 | Turmeric oil (50 mg/kg) n=5 | Turmeric oil (100 mg/kg) n=5 |
| Ear twitch | 47.2 ± 6.3 | 67.7 ± 12.1 | 88.7 ± 15.4 |
| Myoclonic twitch | 58.9 ± 7.6 | 90.9 ± 23.4 | 108.8 ± 19.6 |
| Tail twitch | 58.9 ± 7.6 | 90.9 ± 23.4 | 101.6 ± 8.6 |
| Forelimb clonus | 74.5 ± 15.9 | 103.0 ± 18.5 | 147.6 ± 23.5 |
| Falling | 61.8 ± 10.7 | 86.2 ± 23.8 | 108.0 ± 20.3 |
| Tonic hindlimb extension | 105.6 ± 22.7 | 157.4 ± 35.8 | 208.4 ± 26.4 |
| Death | 128.8 ± 27.1 | 188.6 ± 36.2 | 237.8 ± 23.9 |
A
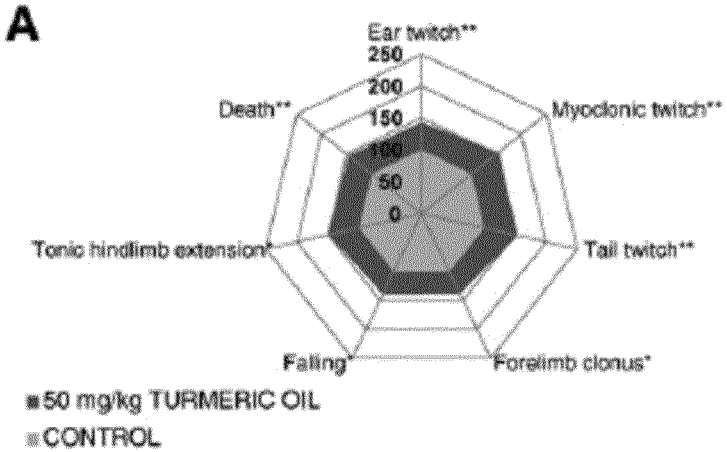
B
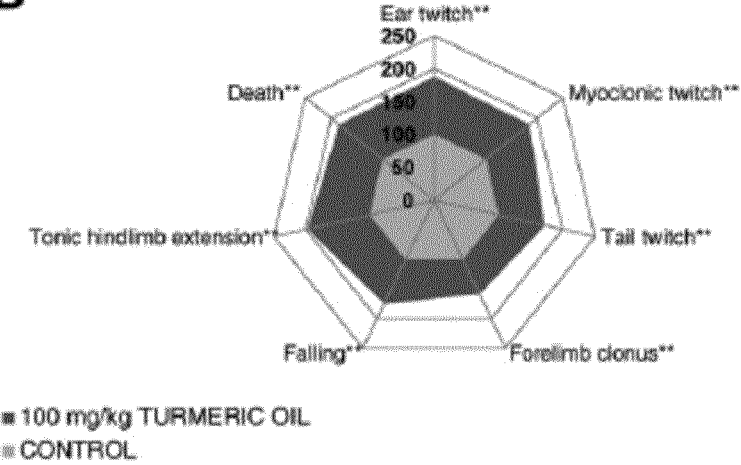

Figure 10

| Seizure parameters | PTZ dose required to elicit individual seizure parameters (mg/kg) | | | |
|---|---|---|---|---|
| | Control A (vehicle) n=5 | AB-turmerone (100 mg/kg) n=5 | Control B (vehicle) n=5 | Ar-turmerone (50 mg/kg) n=5 |
| Ear twitch | 56.7 ± 11.4 | 98.3 ± 30.7 | 44.6 ± 11.6 | 70.5 ± 11.8 |
| Myoclonic twitch | 59.0 ± 11.2 | 112.6 ± 36.2 | 48.3 ± 11.7 | 74.1 ± 14.2 |
| Tail twitch | 58.0 ± 10.3 | 97.5 ± 30.0 | 48.3 ± 11.7 | 73.5 ± 13.9 |
| Forelimb clonus | 89.3 ± 12.1 | 137.4 ± 35.3 | 61.5 ± 11.0 | 121.7 ± 15.4 |
| Falling | 80.6 ± 17.1 | 140.2 ± 50.7 | 57.1 ± 15.8 | 95.5 ± 21.4 |
| Tonic hindlimb extension | 98.7 ± 22.5 | 215.2 ± 36.0 | 98.7 ± 23.3 | 131.5 ± 15.3 |
| Death | 122.1 ± 23.2 | 226.1 ± 30.2 | 122.1 ± 20.5 | 195.6 ± 49.2 |

A

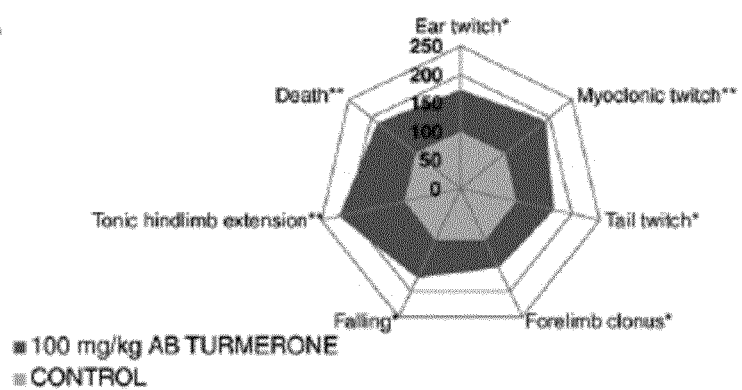

■ 100 mg/kg AB TURMERONE
■ CONTROL

B

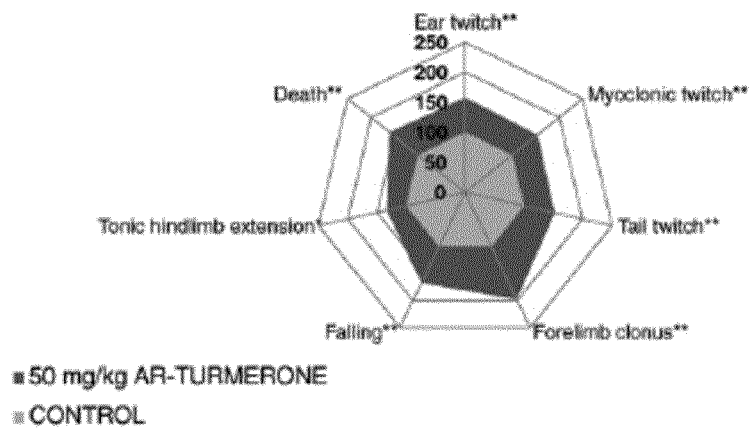

■ 50 mg/kg AR-TURMERONE
■ CONTROL

Figure 11
A
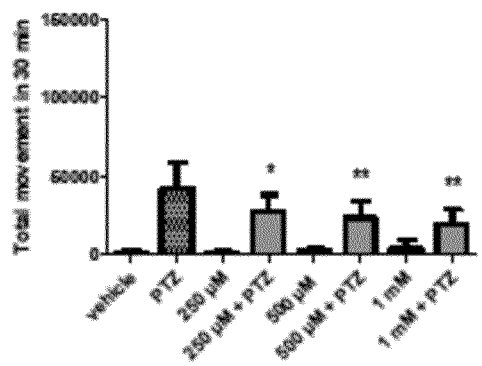
B
| | PTZ dose required to elicit individual seizure parameters (mg/kg) | |
|---|---|---|
| Seizure parameters | Control (vehicle) n=5 | Sodium valproate (50 mg/kg) n=5 |
| Ear twitch | 56.7 ± 11.4 | 67.8 ± 23.6 |
| Myoclonic twitch | 59.0 ± 11.2 | 72.2 ± 31.2 |
| Tail twitch | 58.0 ± 10.3 | 72.2 ± 31.2 |
| Forelimb clonus | 89.3 ± 12.1 | 98.1 ± 32.4 |
| Falling | 80.6 ± 17.1 | 89.7 ± 39.6 |
| Tonic hindlimb extension | 98.7 ± 22.5 | 143.6 ± 27.1 |
| Death | 122.1 ± 23.2 | 181.5 ± 33.5 |
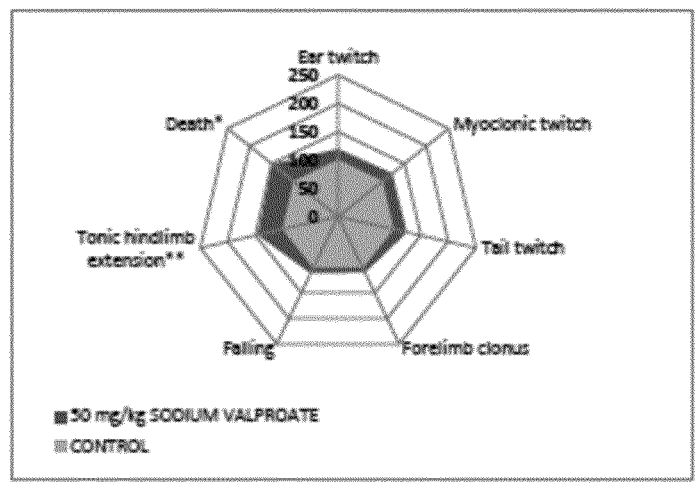

Figure 12
A)
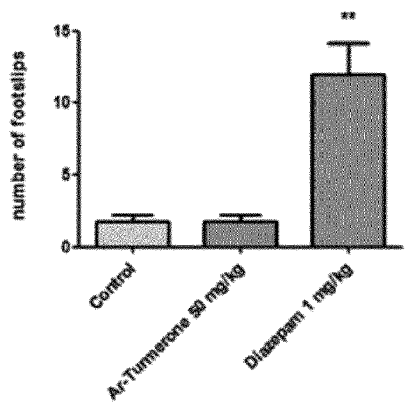
B)
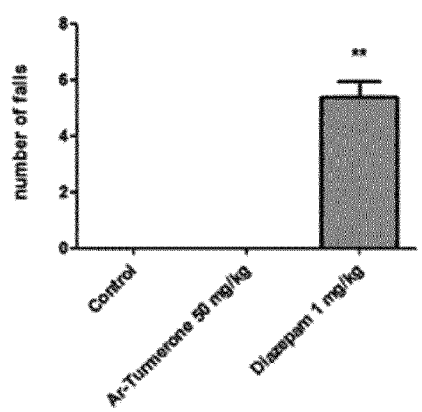
C)
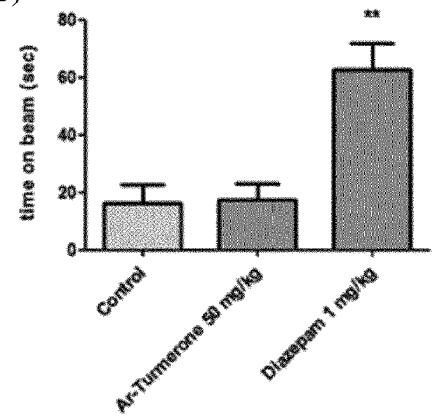

ANTICONVULSANT ACTIVITY OF TURMERIC OIL AND BISABOLENE SESQUITERPENOIDS

FIELD OF THE INVENTION

The present invention relates to the anticonvulsant activity of turmeric oil and its volatile bisabolene sesquiterpenoids ar-turmerone, α-turmerone, β-turmerone (curlone) and α-atlantone, as an anticonvulsant agent for the treatment of epilepsy and/or as a therapeutic agent for the treatment of disorders of the central nervous system, including tremor, pain, mood disorders (including depression, bipolar disorder, attention deficit-hyperactivity disorder, and schizophrenia), and neurodegenerative diseases.

BACKGROUND OF THE INVENTION

Epilepsy is a widespread neurological disorder that affects approximately 50 million people worldwide (1). According to the World Health Organization (WHO), about 1% of the total burden of disease corresponds to various forms of epilepsy. Its pharmacologic treatment comprises a number of currently available antiepileptic drugs (AEDs) (2). The main problem concerning AEDs is the high incidence of side effects ranging from gastrointestinal distress, hepatotoxicity, depression, cognitive impairment and even refractory seizures (2) (3) (4) (5) (6). Moreover, about one third of patients suffering from epilepsy remain resistant to available treatments (1) (2). Hence, there is a clear need to continue to identify novel AEDs that control seizures with minimal adverse effects.

Medicinal plants and the chemical compounds contained therein represent a potential source of novel AEDs. Numerous studies on the use of ethnomedicinal plants for the treatment of seizures have been reported (7). Small molecule compounds and essential oils extracted from plants have been shown to exhibit anticonvulsant properties (18) (19) (20). One compound, losigamone, derived from the kava kava plant and originally used by traditional healers in the South Pacific as an anxiolytic, is now in early clinical development as a novel antiepileptic drug (8) (9). Another plant, *Curcuma longa* L., is a medicinal perennial herb of the Zingiberaceae family native to South Asia. It has been traditionally used as a carminative, laxative, anthelmintic and as a treatment for liver disorders. The powder of its rhizomes, turmeric, has been used not only as a condiment and color additive in food but also in traditional medicine against epilepsy (10). Its major active chemical constituents are the curcuminoids (3-5%) and the volatile turmeric oil (2-7%). Turmeric oil is mainly composed of bisabolene sesquiterpenoids: ar-, α-, β-, turmerone, α-atlantone and curlone, whereas the curcuminoids include curcumin, monodemethoxycurcumin and bisdemethoxycurcumin. Nearly all investigations on the medicinal properties of turmeric have been focused on curcumin, whose anticonvulsant activities have been demonstrated in several rodent models such as the iron-induced epileptogenesis (11), maximal electroshock (12), kainic acid-induced (13) and pentylenetetrazole-kindling (14) models. However, while a few studies on the neuroprotective activity of turmeric oil have been performed (15) (16) (17), a specific link between anticonvulsant activity and non-curcuminoid compounds such as volatile turmeric oil or bisabolene sesquiterpenoids has not been evaluated. Notably, previous studies on the volatile constituents of turmeric oil were limited due to the complex isolation steps involved.

Described herein is a practical method to isolate the main constituents of turmeric oil through RP-HPLC. The isolated compounds were individually evaluated in two vertebrate model systems: the zebrafish (*Danio rerio*) and the mouse (*Mus musculus*). Over the past decade, the zebrafish has emerged as a valuable model for genetic studies and drug screening. The strength of this in vivo model relies on its high genetic, physiologic and pharmacologic homology to humans. Their high fecundity and small size allow for the performance of tests in a medium- to high-throughput fashion using minute (microgram-scale) quantities of compound. The zebrafish also holds promise as an in vivo model for identifying novel neuroactive compounds since the dopaminergic, serotonergic, and GABAergic systems develop early during embryogenesis and are already functional in larvae (21). In addition, their rapid development ex utero and optical transparency makes it possible to easily detect morphological and behavioral effects of test compounds on living embryos and larvae (22).

More recently, zebrafish have also proven useful for the primary screening of potential novel anticonvulsants (23) (24) (25). An acute zebrafish seizure model based on the proconvulsant pentylenetetrazole (PTZ) has been described (23). The exposure of zebrafish larvae to PTZ evoked a sequence of behavioral changes, which were classified into three phases: a notable increase in swimming activity (stage I); rapid "whirlpool-like" circular swimming motion (stage II), and clonic movements with subsequent loss of posture and loss of movement for 1-3 seconds followed by tonic contractions (stage III) (23). In addition, electrophysiological recordings confirmed that zebrafish larval brains treated with PTZ displayed a series of ictal and interictal discharges. A follow-up study validated this zebrafish chemoconvulsant model by showing that 13 out of 14 clinically used AEDs were capable of suppressing PTZ-induced seizure behaviors in zebrafish (24).

In the course of screening a series of medicinal plants for their potential anticonvulsant activities in the zebrafish PTZ chemoconvulsant model, we confirmed the reported anticonvulsant properties of curcumin. Surprisingly, however, further testing of turmeric oil and its chromatographic fractions revealed additional constituents capable of suppressing PTZ-induced seizure behaviors in larval zebrafish. Mass spectrometry and NMR analysis of these active purified fractions revealed them to belong to the bisabolene sesquiterpenoids ar-turmerone, α-, β-turmerone (curlone) and α-atlantone. The anticonvulsant activities identified using the zebrafish PTZ assay were then confirmed in the equivalent mouse PTZ-induced seizure model and the 6 Hz psychomotor seizure model of partial epilepsy. Additionally, an assessment on motor coordination and balance was performed jn mice using the elevated bridge after i.v. injection of ar-turmerone in order to determine any side effects leading to motor impairment.

There have been some publication providing turmeric extracts, for use in medicine, however, none of them provides the use thereof as an anticonvulsant agent in the treatment of disorders of the central nervous system. For example WO2007109210 and WO2010045577 provide extracts of *curcuma* plants, and methods of treating neurodegenerative disorders such as disorders associated with amyloid plaque aggregation or fibril formation (e.g. Alzheimer's disease), however, neither patent application discloses or suggests a potential use of *curcuma* extracts as anticonvulsant agents. WO2011080090 provides formulations of turmeric oil having anti-inflammatory, analgesic and/or anti-cancer activities, however, again it neither discloses nor suggests a potential use of *curcuma* extracts as anticonvulsant agents.

Even more, it is known that bisabolene-type sesquiterpenoids exhibit Acetylcholine esterase inhibitory activity (41), whereas it has also been shown that AChE blockers, in general induce seizures and may lead to status epilepticus, resulting in spontaneous seizures following a latent period (42). It was therefore surprising to find that bisabolene-type sesquiterpenoids are in fact capable of reducing the extent of epileptic seizures, rendering them suitable as anticonvulsant agents in the treatment of central nervous system disorders.

SUMMARY OF THE INVENTION

A first aspect of the present invention relates to a bisabolene sesquiterpenoid for use as an anticonvulsant agent in disorders of the central nervous system. In some embodiments, the present invention relates to a bisabolene sesquiterpenoid of turmeric oil for use as an anticonvulsant agent in disorders of the central nervous system. The turmeric oil may be from a *Curcuma* genus in particular *Curcuma longa* L.

In a certain embodiment, the bisabolene sesquiterpenoid according to this invention is selected from the list comprising ar-turmerone, α-turmerone, β-turmerone and α-atlantone. In a further aspect, the present invention provides a liquid composition comprising one or more bisabolene sesquiterpenoids according to this invention; for use as an anticonvulsant agent in disorders of the central nervous system. In a preferred embodiment, the liquid composition according to this invention is turmeric oil from a *Curcuma* genus in particular *Curcuma longa* L.

In a further aspect, the invention relates to bisabolene sesquiterpenoids or a composition comprising one or more bisabolene sesquiterpenoid for use as a therapeutic agent for the treatment of disorders of the central nervous system; wherein said disorders are selected from the list comprising: epilepsy, tremor, pain, mood disorders and neurodegenerative diseases; in particular epilepsy. Said mood disorders can be depression, bipolar disorder, attention deficit-hyperactivity disorder, and schizophrenia. Said neurodegenerative disorders might not include Alzheimer's disease.

Preferably, said disorders of the central nervous system are not cerebrovascular disorders. With cerebrovascular disorders are meant the disorders indicated as cerebrovascular disorders in patent application WO03/051380 published on 26 Jun. 2003. Hence, with "cerebrovascular disorder" is meant a disorder selected from a group comprising ischaemia, stroke, post-stroke injury, hemorrhage, reperfusion injury, thrombosis, vasoconstriction, nitric oxide-induced free radical oxidative damage, infraction, inflammation, and Alzheimer's disease.

BRIEF DESCRIPTION OF THE FIGURES

FIG. 1. Schematic diagram of the videotracking procedure in a 96-well plate using 7-dpf zebrafish larvae for the anticonvulsant activity evaluation (FIG. 1A). The plate was incubated in dark conditions inside the zebrabox with 100 μL vehicle or drug and one larvae per well. After 1 hour of incubation, 100 μL of vehicle of PTZ was added to the first and second wells respectively in order to monitor larval behavior in presence of the vehicle/compound and the proconvulsant for 30 minutes. FIG. 1B shows the zebrabox, core system, and larval behavior screen.

Summary of the evaluation of the anticonvulsant activity of turmeric in the zebrafish PTZ seizure assay (C) Turmeric methanolic extract; (D) curcuminoids and (E) turmeric oil. Tested concentrations are indicated along the x-axis, and the total gross locomotor activity exhibited by zebrafish larvae within 30 min is displayed along the y-axis. Data are expressed as the mean±SD (n=10-12). Statistically significant differences between vehicle-treated and sample-treated (white bars) or PTZ-treated and sample plus PTZ-treated groups (gray bars) are labeled as * for $p<0.05$ and ** for $p<0.01$.

FIG. 3: Evaluation of the anticonvulsant effects of phenytoin (A) and diazepam (B), which served as positive controls for the PTZ-induced zebrafish acute seizure model.

Figure 4:
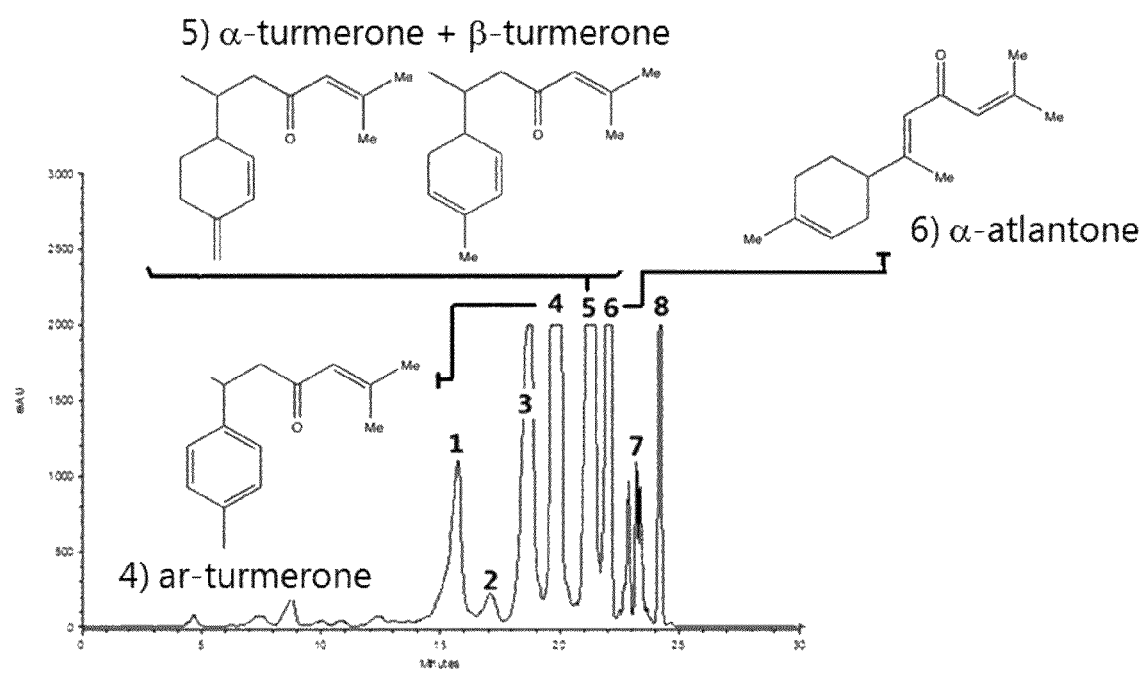

FIG. 4: HPLC chromatogram of turmeric oil and its major constituents. Peak 4 corresponds to A) ar-turmerone; peak 5 to B) α-turmerone and β-turmerone (curlone) and peak 6 to C) α-atlantone.

Figure 5:
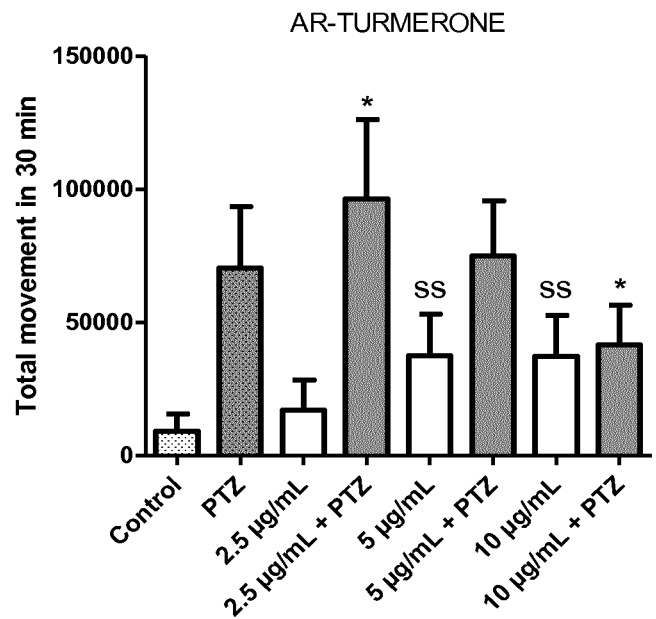

FIG. 5: Anticonvulsant activity evaluation of ar-turmerone: The x-axis represents the type of treatment. The y-axis indicates the total distance moved in 30 minutes. For PTZ group, statistical significance is identified as * for $p<0.05$ and ** for $p<0.01$; control group is indicated with s for $p<0.05$ and ss for $p<0.01$.

Figure 6:
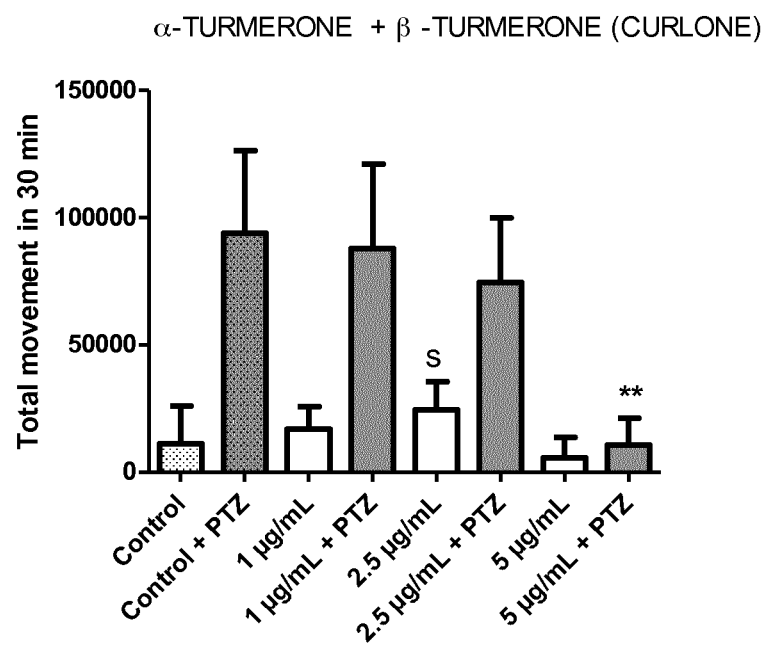

FIG. 6: Anticonvulsant activity evaluation of α-turmerone and β-turmerone (curlone). The x-axis represents the type of treatment. The y-axis indicates the total distance moved in 30 minutes. For PTZ group, statistical significance is identified as * for $p<0.05$ and ** for $p<0.01$; control group is indicated with s for $p<0.05$ and ss for $p<0.01$.

Figure 7:
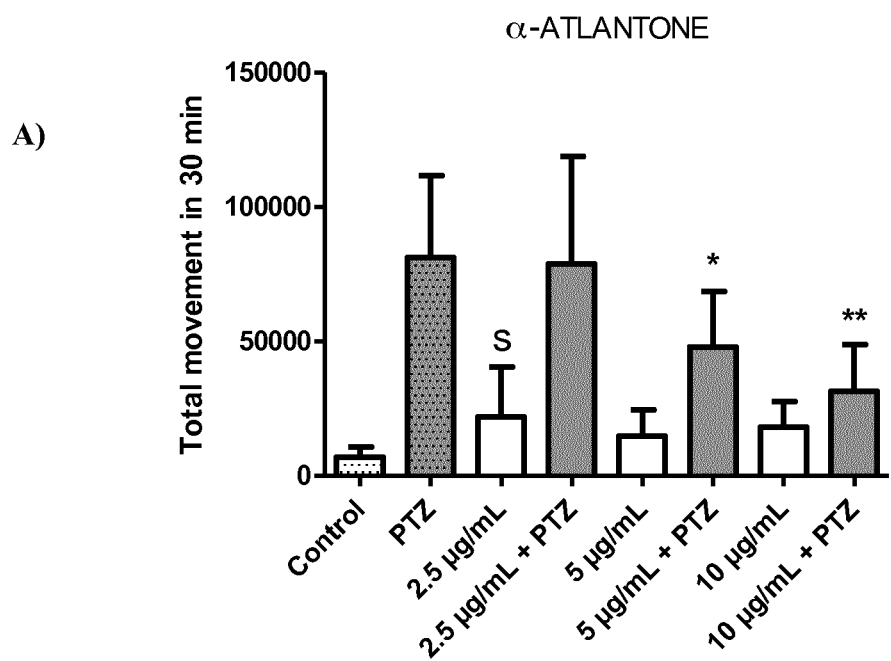
Figure 7:
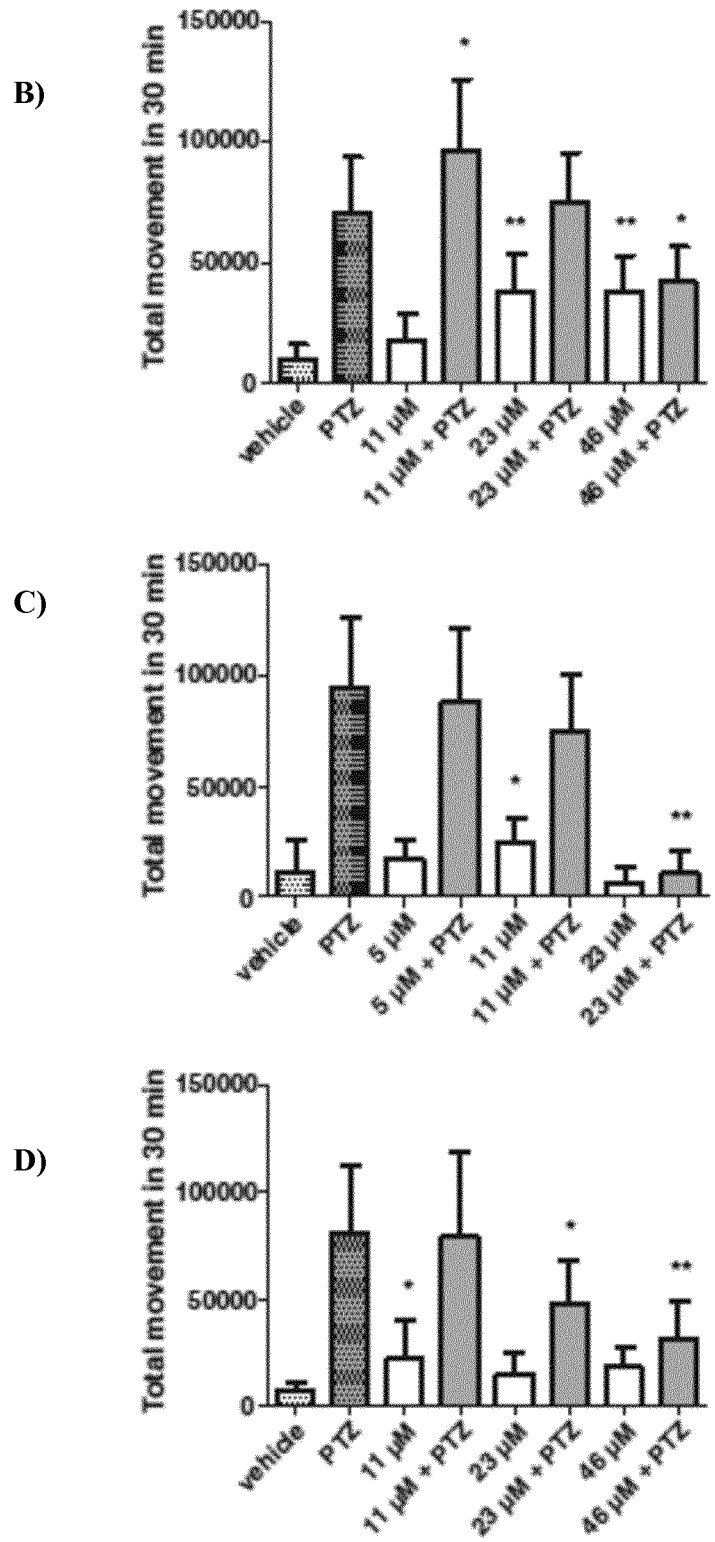

FIG. 7: Anticonvulsant activity evaluation of α-atlantone. (A) The x-axis represents the type of treatment. The y-axis indicates the total distance moved in 30 minutes. For PTZ group, statistical significance is identified as * for $p<0.05$ and ** for $p<0.01$; control group is indicated with s for $p<0.05$ and ss for $p<0.01$.

Summary of evaluation of the anticonvulsant activity of bisabolene sesquiterpenoids in the zebrafish PTZ seizure assay. (B) Ar-turmerone; (C) α,β-turmerone and (D) α-atlantone. The x-axis represents the tested concentration for each one of the sesquiterpenoids. The y-axis indicates the total gross locomotor activity exhibited by zebrafish larvae within 30 min. Data are expressed as the mean±SD (n=10-12). Statistically significant differences between vehicle-treated and sample-treated (white bars) or PTZ-treated and sample plus PTZ-treated groups (gray bars) are labeled as * for $p<0.05$ and ** for $p<0.01$.

FIG. 8: Anticonvulsant activity of turmeric oil and ar-turmerone in the mouse PTZ-induced seizure assay. Graphs depict the dose of PTZ required to evoke various seizure behaviors. The PTZ dose for control is set to 100% (inner heptagons in A and B) and results obtained with turmeric oil (outer heptagon in A) and ar-turmerone (outer heptagon in B) are depicted relative to control. Statistical significance between control and experimental PTZ doses required to induce each seizure behavior were calculated using the unpaired Student's t-test. Statistical significance vs. controls is labeled as (*) for $p<0.05$ and (**) for $p<0.01$.

FIG. 9. Evaluation of the anticonvulsant activity of turmeric oil in the mouse PTZ seizure model. Top panel: table listing PTZ dose/s required to elicit the indicated seizure behaviors after treatment with turmeric oil or vehicle only.

Data are expressed as the mean±SD (n=5). Graphical depiction of tabulated results from (A) turmeric oil at 50 mg/kg and (B) at 100 mg/kg. Results are expressed as relative values compared to control (set as 100%). Statistically significant differences between sample (dark gray) and control group (light gray) are labeled as * for pb0.05 and ** for pb0.01 (unpaired Student's t-test). For sake of clarity, SDs are not depicted in the graphs but are indicated in the tables. However, the coefficient of variation never exceeded 28% (unpaired Student's t-test).

FIG. 10. Evaluation of the anticonvulsant activities of α,β-turmerone and ar-turmerone in the mouse PTZ seizure model. Top panel: table listing PTZ dose/s required to elicit the indicated seizure behaviors after treatment with bisabolene sesquiterpenoid or vehicle only. Graphical depiction of tabulated results from (A) α,β-turmerone at a dose of 100 mg/kg and (B) ar-turmerone at 50 mg/kg. 'Control A' column corresponds to vehicle-treated controls for α,β-turmerone; 'Control B' column corresponds to vehicle-treated controls for ar-turmerone. Data are expressed as the mean±SD (n=5). For sake of clarity, SDs are not depicted in the graphs but are indicated in the tables. Results are expressed as relative values compared to control (set as 100%). Statistically significant differences between sample (dark gray) and control group (light gray) are labeled as * for $p<0.05$ and ** for $p<0.01$ (unpaired Student's t-test). For the sake of clarity, SDs are not depicted. However, the coefficient of variation never exceeded 28% and 37% in the case of ar-turmerone and α,β-turmerone, respectively.

FIG. 11. Evaluation of the anticonvulsant activity of sodium valproate (positive control) in the zebrafish and mouse PTZ seizure assays. (A) Zebrafish PTZ assay. The x-axis represents the concentration of the sodium valproate evaluated. The y-axis indicates the total gross locomotor activity exhibited by zebrafish larvae within 30 min. Data are expressed as the mean±SD (n=10-12). Statistically significant differences between vehicle-treated and sample-treated (white bars) or PTZ-treated and sample plus PTZ-treated groups (gray bars) are labeled as * for $p<0.05$ and ** for $p<0.01$. (B) Mouse PTZ assay. Top panel: table listing PTZ dose/s required to elicit the indicated seizure behaviors after treatment with sodium valproate or vehicle only. Lower panel: graphical depiction of tabulated results from treatment with sodium valproate at a dose of 50 mg/kg. Results are expressed as relative values compared to control (set as 100%). Significant differences between sodium valproate (dark gray) and control group (light gray) are labeled as * for $p<0.05$ and ** for $p<0.01$ (unpaired Student's t-test). For the sake of clarity, SDs are not depicted. However, the coefficient of variation never exceeded 45%.

FIG. 12. Data set from the C57B1/6 male mice after i.v. injection of vehicle (negative control), diazepam 1 mg/kg (positive control), and ar-turmerone 50 mg/kg on the elevated bridge apparatus. Measures of number of footslips (A), number of falls (B) and total time on beam (C) are showed. Diazepam was selected as positive control due to its well-know motor impairment side effect after i.v/i.p administration in mice.

Figure 13:
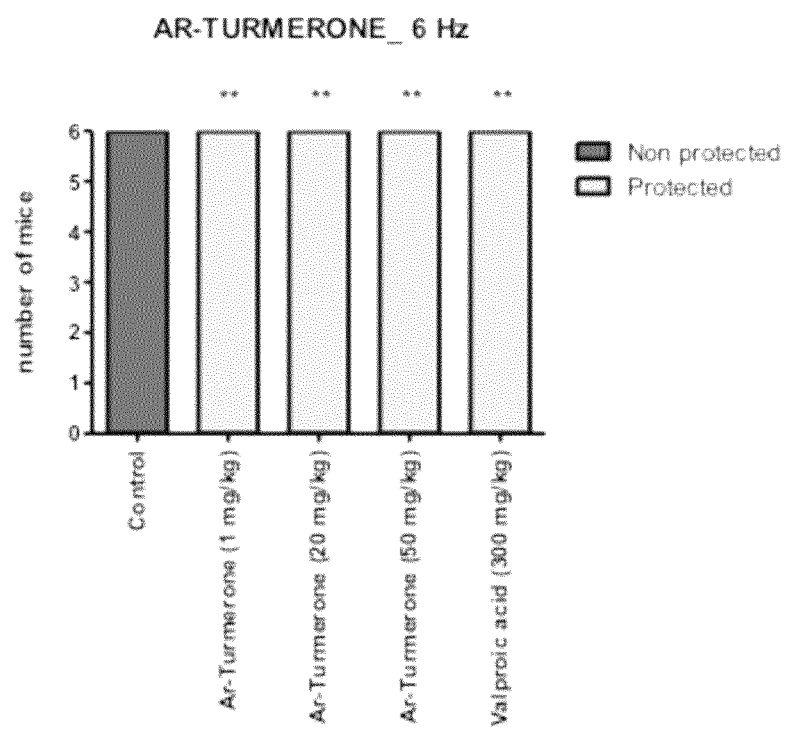

FIG. 13. Evaluation of the protective activity of ar-turmerone in the 6-Hz model. Vehicle (negative control) and valproic acid 300 mg/kg (positive control) were included in the assessment. Data points indicate the number of animals protected from seizures at the corresponding dose (n=6).

DETAILED DESCRIPTION OF THE INVENTION

A first aspect of the present invention relates to a bisabolene sesquiterpenoid for use as an anticonvulsant agent in disorders of the central nervous system. One or more bisabolene sesquiterpenoids may be used either alone or in combination. The bisabolene sesquiterpenoids may be a sesquiterpenoid of turmeric oil. In some embodiments, the bisabolene sesquiterpenoids are isolated from turmeric oil. The Curcuma longa L plant may be a source for turmeric oil and/or bisabolene sesquiterpenoids. Other sources for bisabolene sesquiterpenoids include, but are not limited to, essential oils from plants (for example Peltphorum dasyrachis Kurz ex Bakar (Yellow Batai)), insects, natural products produced by living organisms (for example, honeycomb extract), fungi, bacteria, and/or microorganisms. Bisabolene sesquiterpenoids may also be produced via chemical synthesis.

"Bisabolenes" are a group of closely related natural chemical compounds which are classified as sesquiterpenes (a class of terpenes consisting of three isoprene units). Biochemical modifications such as oxidation or rearrangement produce the related sesquiterpenoids.

The term "turmeric" is also interchangeable with "curcuma" and includes plants, clones, variants and sports from the plant Zingiberaceae family. In particular, turmeric includes plants, clones, variants and sports from the plant genus Curcuma; more in particular Curcuma longa L. Therefore, in a preferred embodiment, the turmeric oil is from a Curcuma genus in particular Curcuma longa L. Turmeric, and in particular its rhizomes, contains about 3-5% of curcuminoids, such as curcumin and about 2-7% of turmeric oil. A "rhizome" is a stem of a plant which is usually found underground, often sending out roots and shoots from its nodes.

"Turmeric oil" can be obtained as detailed herein below in the examples, such as by hydro-distillation of dried rhizome powder of Curcuma. However, it may also be obtained via any other suitable way. Turmeric oil is mainly composed of bisabolene sesquiterpenoids: ar-turmerone, α-turmerone, β-turmerone and α-atlantone, and thus in a particular embodiment, the present invention provides ar-turmerone, α-turmerone, β-turmerone and/or α-atlantone for use as an anticonvulsant agent in disorders of the central nervous system. In certain embodiments, ar-turmerone, α-turmerone, β-turmerone, and α-atlantone are administered singly. In some embodiments, ar-turmerone is administered in combination with α-turmerone, β-turmerone, and/or α-atlantone. Ar-turmerone may also be adminstered with one or more of turmerone, β-turmerone, and/or α-atlantone. In certain embodiments, α-turmerone is administered in combination with ar-turmerone, β-turmerone and/or α-atlantone. α-turmerone may also be administered in combination with one or more of ar-turmerone, β-turmerone and/or α-atlantone. In some embodiments, β-turmerone is administered in combination with ar-turmerone, α-turmerone, and/or α-atlantone. β-turmerone may be administered in combination with one or more of ar-turmerone, α-turmerone, and/or α-atlantone. In certain embodiments, α-atlantone may be administered in combination with ar-turmerone, α-turmerone, and/or β-turmerone. α-atlantone may be administered in combination with one or more of ar-turmerone, α-turmerone, and/or β-turmerone. When two or more compounds are administered, the administration may be simultaneous or serial.

Turmeric oil and/or bisabolene sesquiterpenoids are lipophilic and cross the blood-brain barrier and other cell membranes, a quality which may enhance bioavailability of the compounds in the nervous system. Thus, the use of tumeric oil and/or bisabolene sesquiterpenoids confers advantages over the use of other compounds such as curcumin. Curcumin is also a component of the *Curcuma longa* L plant, and a compound to which the anticonvulsant activity of *Curcuma* has been attributed (11) (12) (32). However, certain formulations of curcumin are readily converted to water soluble metabolites in the intestines and excreted, so that little of the compound reaches the blood or the nervous system.

The term "anticonvulsant agent" as used herein is meant to include any compound suitable for the treatment of epileptic seizures, bipolar disorders, mood disorders and/or neuropathic pain. Epileptic seizures may result from any abnormal, excessive, or hypersynchronous neuronal activity in the brain. In some embodiments, epileptic seizures which require treatment with anticonvulsants are caused by infection, stroke, trauma, fever, tumors, drug use, damage to the blood-brain barrier, and/or neurodegenerative disease. In certain embodiments, epileptic seizures are triggered by emotional state, by response to light and/or sound, sleep, sleep deprivation, hormones, metabolic disorders, and/or congenital defects. Epileptic seizures for which the anticonvulsants disclosed herein provide treatment may be classified as partial seizures, such as simple partial seizures and/or complex partial seizures, or they may be classified as generalized seizures, such as absence seizures, myoclonic seizures, clonic seizures, tonic seizures, tonic-clonic seizures, and/or atonic seizures, or a mixed seizure. The anticonvulsants described herein, such as turmeric oil, ar-turmerone, α-turmerone, β-turmerone and/or α-atlantone, may also provide treatment for therapy-resistant forms of seizure. Notably, the 6 Hz psychomotor seizure model of partial epilepsy has been used as a model therapy-resistant forms of seizures, including limbic seizures (40).

Patients suffering from epileptic seizures may be infants aged 0-6 months, 6-12 months, 12-18 months, 18-24 months. In certain embodiments, patients suffering from epileptic seizures are individuals aged 65-70, 75-80, 85-90, 95-100, 100-105, and older. Patients may also be children aged 2-12, adolescents aged 13-19, or adults aged 20-64.

Anticonvulsants may be used for the treatment of epileptic seizures, including treatment of symptoms associated with epileptic seizures and/or epilepsy. Anticonvulsants may also be used to treat epileptic seizures that result from central nervous system disorders such as cerebrovascular diseases and/or neurodegenerative diseases. One goal of an anticonvulsant agent (i.e., an "anticonvulsant") is to suppress the rapid and excessive firing of neurons that start a seizure. Another goal of an anticonvulsant is to prevent the spread of the seizure within the brain and offer protection against possible excitotoxic effects, that may result in brain damage. Anticonvulsants are also called antiepileptic drugs (abbreviated "AEDs"), and are sometimes referred to as antiseizure drugs. In epilepsy, an area of the brain and/or nervous system is typically hyper-irritable. Antiepileptic drugs function to help reduce this area of irritability and thus prevent epileptic seizures.

The term "central nervous system disorder" is meant to include any disease or disorder of the central nervous system (CNS) including epilepsy, tremor, pain, mood disorders (including depression, bipolar disorder, attention deficit-hyperactivity disorder, schizophrenia); infections of the CNS (e.g. encephalitis), neurodegenerative diseases (e.g. amyothrophic lateral sclerosis, Parkinson's Disease), auto-immune and inflammatory diseases (e.g. multiple sclerosis) and genetic disorders (e.g. Huntington's diseases); in particular epilepsy. In a particular embodiment, the neurodegenerative disorders of the present invention do not include Alzheimer's Disease. In some embodiments, Alzheimer's Disease and/or other neurodegenerative diseases lead to epileptic seizures, which may be treated using anticonvulsants as described herein.

The present invention further provides a liquid composition comprising one or more bisabolene sesquiterpenoids according to this invention; for use as an anticonvulsant agent in disorders of the central nervous system. In a particular embodiment, said liquid composition is turmeric oil from a *Curcuma* genus in particular *Curcuma longa* L.

The liquid composition according to this invention in particular comprises an effective amount of bisabolene sesquiterpenoids. As evident for a person skilled in the art, said effective amount may vary depending on the number and type of bisabolene sesquiterpenoids used. For example turmeric oil as a liquid composition may be used pure or further diluted to a concentration of about 1-50 µg/ml, more in particular about 2.5-20 µg/ml, in particular about 10 µg/ml. Ar-turmerone, α-turmerone, β-turmerone and α-atlantone either or not in combination with each other may for example be present at a concentration of about 11-46 µM, more in particular about 23-46 µM.

These liquid compositions may be formulated and administered systemically or locally. Techniques for formulation and administration may be found in the latest edition of "Remington's Pharmaceutical Sciences" (Mack Publishing Co. Easton Pa.). Suitable routes may, for example, include oral or transmucosal administration as well as parenteral delivery, including intramuscular, subcutaneous, intramedullary, intrathecal, intraventricular, intravenous, intraperitoneal, or intranasal administration.

In a further embodiment, the compositions may be in the form of nutritional or dietary supplements, including tablets, capsules, gels, pastes, emulsions, solutions, caplets, and the like.

EXAMPLES

Having provided a general disclosure, the following examples help to illustrate the general disclosure. These specific examples are included merely to illustrate certain aspects and embodiments of the disclosure, and they are not intended to be limiting in any respect.

Certain general principles described in the examples, however, may be generally applicable to other aspects or embodiments of the disclosure.

Example 1

Materials and Methods

Chemicals and Reagents

Dimethyl sulphoxide (99.9%, spectroscopy grade) was procured from Acros Organics (Belgium); diethyl ether (99.9%, spectroscopy grade) from Aldrich Chemical; and acetonitrile (100%, HPLC grade) from Fisher Scientific (UK). Double-distilled water (ddH$_2$O) was obtained from the Milli-Q purification system.

The curcuminoid mixture from turmeric (curcumin 98%, demethoxycurcumin and bisdemethoxycurcumin) and phenytoin was procured from Acros Organics. PTZ was obtained from Sigma-Aldrich (Germany) and diazepam from Roche.

Plant Material

Dried rhizome powder of *Curcuma longa* L. (turmeric) was acquired from a local supplier in Belgium with India as the source of origin. Microscopic authentication was completed by a research fellow: R. Ansalloni, Universidad de Cuenca, Cuenca, Ecuador (26).

Experimental Animals

All procedures for animal experiments were performed in accordance with the European and National Regulations and approved by the Animal Care and Use Committee of the Katholieke Universiteit Leuven.

Zebrafish (*Danio rerio*)

Adult zebrafish of the Tg (fli 1a: EGFP)y1 strain were reared at 28.5° C. on a 14/10 hour light/dark cycle. Eggs were collected from natural breeding and fostered in embryo medium (17 mM NaCl, 2 mM KCl, 1.8 mM $Ca(NO_3)_2$, 0.12 mM $MgSO_4$, 1.5 mM HEPES buffer pH 7.1-7.3 and 0.6 µM methylene blue) in an incubator at 28.5° C. Sorting of zebrafish embryos and larvae and medium refreshment were performed every day until 7 dpf. All larvae were sacrificed through administration of an overdose of anesthetic (tricaine).

Mice (*Mus musculus*)

Male C57B1/6 mice (20-30 g) from 8 weeks of age were housed in appropriate cages under 12/12 hour light/dark cycle at 28° C. in a quiet room. The animals were fed ad libitum with a pellet diet and water until they were 10 to 12 weeks old.

Example 2

Distillation of Turmeric Essential Oil

Volatile oil from turmeric was obtained by hydro-distillation using a Clevenger-type apparatus according to the European Pharmacopoeia. Turmeric sample (100 g) was extracted with 2 liters of $ddH_2O$ for 3 hours. Four hydro-distillations (400 g) were completed obtaining the pale yellowish and odoriferous oil (yield 2.14%). Turmeric oil was dried over anhydrous sodium sulphate and stored at 4° C. until used.

Example 3

RP-HPLC Analysis of Turmeric Oil and Isolation of its Constituents

Sample of turmeric oil (334 mg) was dissolved in 10 ml of acetonitrile. The injection volume was 300 µl. RP-HPLC analysis of turmeric oil and the subsequent isolation of its constituents were adapted from the original work of He and colleagues (27). RP-HPLC analysis was performed on a high performance liquid chromatographer (LaChrom Elite HPLC System, VWR Hitachi) equipped with diode array detection (DAD) system. RP-HPLC separation of turmeric oil constituents on a preparative scale was achieved using Econosphere 10 µm C18 (250 mm×10 mm) reversed phase column (Grace Davison Discovery Sciences, Belgium) attached to an Econosphere 10 µm C18 (33 mm×7 mm) guard column (Grace Davison Discovery Sciences, Belgium). The column operated at a flow rate of 5 ml/min at room temperature. The profile of the gradient elution was: double-distilled water ($ddH_2O$) (A) and acetonitrile (B); 0-15 min, 40-60% B; 15-20 min, 60-100% B; 20-25 min, 100% B; 25-30 min, 100-40% B. The analytes were monitored with DAD at 260 nm. Eight fractions were individually collected (FIG. 4). Solvents from the collected fractions were removed by separation between diethyl ether and $ddH_2O$.

The ether phase was dried over anhydrous sodium sulphate and the solvent was removed by passing a slow stream of nitrogen over the sample at room temperature. The concentrated samples were stored at 4° C. until analyzed.

Example 4

Chemical Structure Elucidation of Bisabolene Sesquiterpenes

Nuclear Magnetic Resonance (NMR) Analysis $^1H$ and $^{13}C$ NMR-spectra of fractions 4, 5 and 6 were obtained from Bruker 300 Avance and Bruker 600 Avance II+ equipment using deuterated chloroform as solvent and tetramethylsilane (TMS) as internal standard.

Mass Spectroscopy (MS) Analysis

The LC-MS analysis was performed on an Agilent 1100 system equipped with degasser, quaternary pump, autosampler, UV-DAD detector and thermostatised column module coupled to Agilent 6110 single-quadrupole MS. Data acquisition and quantification were obtained from Agilent LC/MSD Chemstation software. Fractions 4, 5 and 6 were analyzed on a Grace Prevail RP-C18 column 3 µm (150 mm×2.1 mm) at a flow rate of 0.2 ml/min. The LC gradient comprised two solvents: double-distilled water ($ddH_2O$)+ 0.1% formic acid (A) and acetonitrile (B); 0-17 min, 40-60% B; 17-32 min, 60-100% B; 32-55 min, 100% B.

The ESI-MS analysis was completed in a Thermo Electron LCQ Advantage apparatus with Agilent 1100 pump and injection system coupled to Xcalibur data analyzing software.

Example 5

Toxicological Evaluation in Zebrafish Model

The aim of this assay was to determine the range of appropriate concentrations to be tested in zebrafish for the anticonvulsant activity evaluation. Seven-dpf zebrafish were placed into a 24-well plate (tissue culture plate, flat bottom, FALCON®, USA), six larvae per well. They were incubated with different concentrations of a test compound dissolved in 1 ml of embryo medium (1% DMSO). The larvae were examined each hour during the period of 6 hours, and compared to control group to detect the following signs of toxicity: the absence of startle response to plate taps, changes in heart rate or circulation, presence of edema, paralysis and death. Thus, the maximum tolerated concentration (MTC) was defined as the highest concentration at which no signs of toxicity were observed in 6 out of 6 zebrafish larvae within 6 hours of exposure to a test compound.

In addition, the larvae were examined during a period of 24 h in sample and compared to control group to detect toxicity. Thus, the maximum tolerated concentration (MTC) was also defined as the highest concentration at which no signs of toxicity were observed in 6 out of 6 zebrafish larvae within 24 h of exposure to sample.

Example 6

Anticonvulsant Activity Evaluation in Zebrafish PTZ Model

Zebrafish larvae from 7-dpf were tracked using the ViewPoint VideoTrack System for Zebrafish™ (Version 2.3.1.0, ViewPoint, France). The system consists of an infrared light source, a high-resolution digital videocamera to capture larval movements within a defined time period (30 minutes in our experimental set-up) and the software to analyze larval locomotor activity (FIG. 1).

The highest concentration tested corresponds to the previously determined MTC. Zebrafish larvae were placed in a 96-well plate (tissue culture plate, flat bottom, FALCON®, USA); one larva per well. Each row of the plate (12 wells) comprised different treatment groups. Two adjacent rows contain the same compound but received two different treatments: a) first row, embryo medium (DMSO 1%), and b) second row, PTZ 20 mM. The first two rows of the plate (vehicle control group, where vehicle was embryo medium) contained a volume of 100 μl of embryo medium (1% DMSO) per well. The following three test groups (two rows each) contained 100 μl of different concentrations of test compound in embryo medium. The larvae thus treated were incubated at room temperature in dark and quiet conditions for 1 hour. Embryo medium (100 μl) was added to the first rows of each one of the four groups. Likewise, 100 μl of PTZ 40 mM were added to the second rows of each treatment group (final concentration of PTZ: 20 mM). Thus, the movement pattern of the exposed zebrafish larvae was video-tracked and assessed in presence of embryo medium (1% DMSO) and PTZ 20 mM. Videotracking of larval movements was started 5 minutes after addition of embryo medium or PTZ to the wells and was recorded for 30 minutes. A total of 8 wells in each plate were left without larvae (medium only) as a negative control, so that each experimental parameter consisted of an average of 10 to 12 larvae. The tracker software measured three periods of 10 minutes of larvae movement. Results were registered as the average value of the total time of larvae movement during 30 minutes. The figures shown are representative of a series of two similar experiments.

Figure 2:
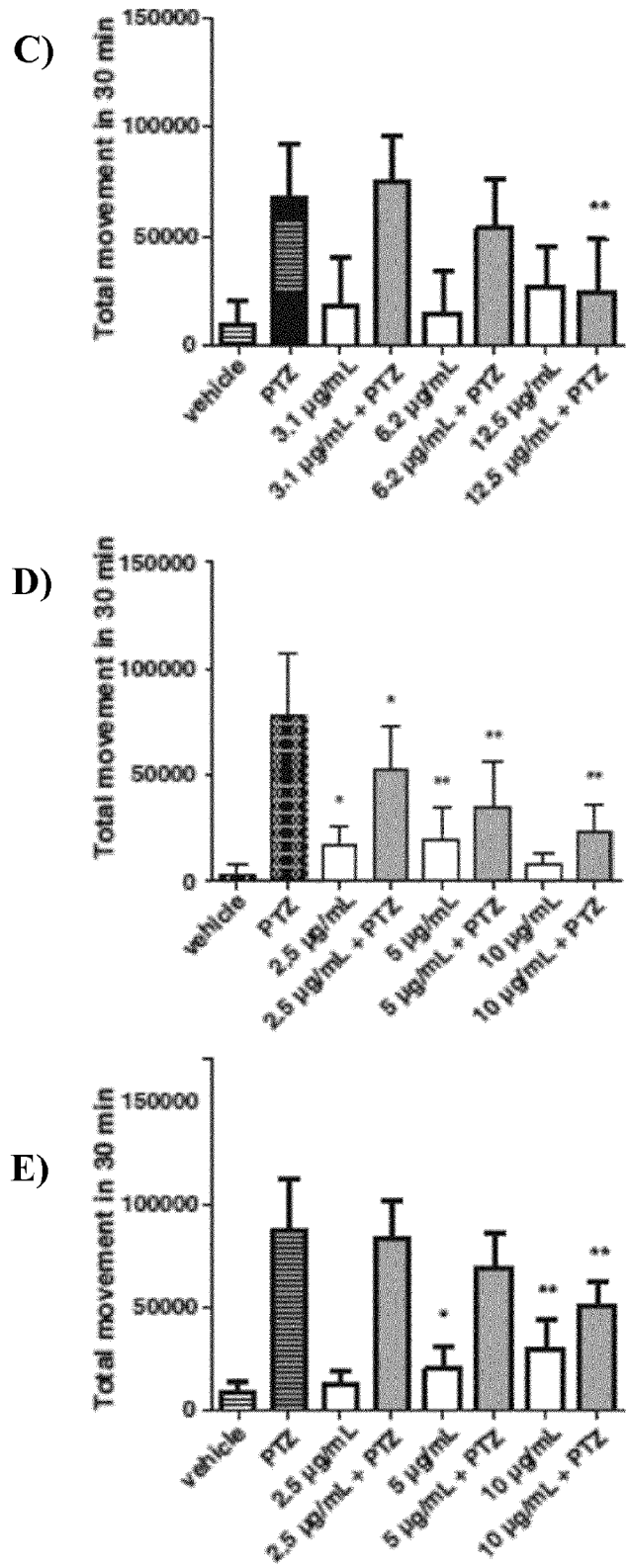
FIG. 2. Comparison of the anticonvulsant activity of A) curcuminoids (curcumin) and B) turmeric oil. Curcumin showed potent activity in inhibiting PTZ-induced seizures ($p<0.05$). Turmeric oil also displayed anticonvulsant activity ($p<0.05$).

The anticonvulsant properties of curcuminoids were assessed through video tracking analysis of seizure-like movements of zebrafish larvae. The higher tested concentrations correspond to MTC, thus in any case larvae did not display any sign of toxicity at these dose. MTC for curcuminoids corresponds to 10 μg/mL. Curcuminoids showed significant anticonvulsant activity ($p<0.05$) at 2.5 μg/mL and at 5 and 10 μg/mL ($p<0.001$) (FIG. 2). This finding is in line with the anticonvulsant properties of curcumin revealed in rodent models (11) (12) (13) (14). On the other hand, further analysis uncovered the anticonvulsant activity for the turmeric oil. The larvae showed significant decrease ($p<0.001$) of PTZ-induced seizures after exposure to turmeric oil (10 μg/ml) (FIG. 2).

The anticonvulsant activity of curcuminoids and turmeric oil was compared to phenytoin and diazepam, two widely used drugs for the treatment of epilepsy. Higher tested concentrations correspond to MTC. Phenytoin showed significant activity at 75 μg/ml ($p<0.05$) and 252.26 μg/ml ($p<0.001$). Diazepam decreased PTZ-induced movements in larvae at the concentrations of 1.42 μg/ml and 14.23 μg/ml ($p<0.001$) (FIG. 3). Curcumin and turmeric oil displayed interesting activity to delay seizure generation at significantly lower concentrations than phenytoin and at equivalent ones of diazepam.

RP-HPLC analysis of turmeric oil revealed eight peaks (FIG. 4). The peaks were individually collected to evaluate the anticonvulsant activity and find the active constituents. Fractions 2 and 7 were not tested in zebrafish model since the collected amounts were not enough for the assay performance. Significant decrease of the seizures triggered by PTZ was observed with fraction 4 ($p<0.05$) at 10 μg/ml, fraction 5 ($p<0.001$) at 5 μg/ml and fraction 6 at concentrations of 5 μg/ml ($p<0.001$) and 10 μg/ml ($p<0.05$) (FIG. 5, FIG. 6, FIG. 7A). The bisabolene sesquiterpenoids exhibited anticonvulsant properties at lower concentrations compared to phenytoin. Fraction 4 and 6 displayed positive response at similar concentrations than diazepam. Fraction 5 was effective at lower concentration than diazepam and phenytoin.

Fractions 4, 5 and 6 that showed positive activity in zebrafish PTZ model were further analyzed for chemical structure elucidation. Retention time, MW and UVmax of fraction 4 are consistent with the product proposed in FIG. 4. $^1$H- and $^{13}$C-NMR spectra of this fraction are in agreement with reported values for ar-turmerone (29), possibly a mixture of enantiomers. NMR analysis indicates that Fraction 5 is a 1:1 mixture of two isomeric structures, possibly mixture of enantiomers. Compounds of this fraction were identified by 1D- and 2D-NMR analysis as α-turmerone and β-turmerone (curlone) (30). Isomerisation to the aromatic analogue ar-turmerone was not observed by NMR after one week. Structure of Fraction 6 was identified as α-atlantone (probably the E-isomer) based on MW, 1D- and 2D-NMR spectra (29) (31) (FIG. 4; Table 1).

TABLE 1

UV and MS data of bisabolene sesquiterpenoids from turmeric oil. The obtained data from analysis is compared with values from the analysis of X.He and colleagues (24) referred between brackets [ ].

| Fraction | Rt (lit.) (min.) | UVmax (lit.) (nm) | Mass Peak | Suggested MW |
|---|---|---|---|---|
| 4 | 24 [25.3] | 238 [238] | 217 | 216 |
| 5 | 27.2 [28.1] | 229 [/]; 238 [238] | 219 | 218 |
| 6 | 29.3 [/] | 195 [/]; 269 [/] | 219 | 218 |

Fraction 4: ar-turmerone;
fraction 5: α,β-turmerone (curlone);
fraction 6: α-atlantone The analysis of the methanolic extract of turmeric (*C. longa* rhizome powder) revealed anticonvulsant activity in the zebrafish larval PTZ assay. In order to identify the active constituents present in the methanolic extract of turmeric, the anticonvulsant properties of curcuminoids and turmeric oil were also assessed through videotracking analysis. Curcuminoids showed anticonvulsant activity at 2.5 μg/ml ($p<0.05$) and at 5 and 10 μg/ml ($p<0.01$) in our larval PTZ assay. Further analysis uncovered an additional anticonvulsant activity for turmeric oil. The larvae showed a decrease ($p<0.01$) of PTZ-induced convulsions after exposure to turmeric oil (10 μg/ml) (FIG. 2C-2E). Notably, exposure of zebrafish larvae to curcuminoids or turmeric oil alone (i.e. in the absence of proconvulsant) also resulted in a slight increase in locomotor activity compared to vehicle-treated controls. However, no obvious signs of toxicity (as measured by change in heart rate, loss of posture, lack or delay in response to tactile stimuli, or death were observed in these larvae.

The anticonvulsant properties of the bisabolene sesquiterpenoids were also assessed through video tracking analysis of seizure-like movements of zebrafish larvae. The higher tested concentrations correspond to MTC, thus in any case larvae did not display any sign of toxicity at these dose. Significant decrease in the convulsions triggered by PTZ was observed for fractions ar-turmerone, α,β-turmerone and α-atlantone. Ar-turmerone showed anticonvulsant activity at 46 μM ($p<0.05$), α-,β-turmerone at 23 μM ($p<0.01$) and α-atlantone at concentrations of 23 μM ($p<0.05$) and 46 μM ($p<0.01$) (FIG. 7B-7D).

Example 7

Generation of PTZ-induced Seizures in Mice

Mice were randomly divided into groups of five animals (vehicle (where vehicle was polyethylene glycol 200 (PEG200):water 1:1) and sample). The animals were pre-warmed under an infrared lamp for 10 minutes to dilate the tail veins. They were then placed in a restrainer and the lateral tail vein was catheterized with 1-cm long, 29-gauge needle. The needle was secured to the tail with surgical tape after confirming a correct placement. The needle was attached to a 0.7-m long polyethylene tubing connected to two 2.5-ml glass syringes containing: a) sample (control vehicle or test compounds) and b) PTZ (7.5 mg/ml ddH2O). These syringes were mounted on an infusion pump (ALA-DOIN-1000 11 VDC, 0.75 Å, World Precision Instruments). Thus, 100 µL of control vehicle (PEG 200: ddH2O 1:1) or test compounds (turmeric oil and ar-turmerone) were IV infused at the rate of 50 µl/min for 2 minutes. Ten minutes later, mice were released from the restrainer and placed in a transparent plastic cage for observation.

PTZ was constantly infused at the rate of 150 µl/min. Seizure manifestation stages in mice were scored according to the time between the start of PTZ infusion and the following behavioral events: ear, tail and myoclonic twitch, forelimb clonus, falling, tonic hindlimb extension and death (28). Behavior was observed up to 5 minutes of PTZ infusion. In case of any surviving mice, they were sacrificed.

PTZ doses were calculated according to the formula: PTZ dose [mg/kg]=(PTZ concentration [mg/ml]×infusion rate [ml/s]×infusion duration [s]×1000)/mouse weight [g]). All work solutions contained heparine (20 µl/ml).

Further evaluation of turmeric oil to control generation of PTZ-induced seizures in mice showed a delay on the onset of seizure parameters in mouse PTZ assay. Mice treated with turmeric oil (50 mg/kg) showed a significant increase in PTZ doses required to trigger all behavioral endpoints: tail twitch ($p<0.001$), ear twitch, myoclonic twitch, forelimb clonus, falling, tonic hind limb extension and death ($p<0.05$) compared to control group (FIG. 8A). Interestingly, ar-turmerone at a dose of 200 mg/kg also showed in mice a significant PTZ dose increase for generating ear, tail and myoclonic twitch, tonic hind limb extension and death ($p<0.05$) as compared to control (FIG. 8B).

When the vehicle PEG200:DMSO 1:1 was used, mice treated with turmeric oil (50 mg/kg) showed a significant increase in PTZ doses required to trigger all behavioral endpoints: forelimb clonus, falling and tonic hindlimb extension ($p<0.05$) and ear, myoclonic, tail twitch, and death ($p<0.01$), compared to control group (FIG. 9A).

Moreover, a dose of 100-mg/kg turmeric oil in the mouse PTZ assay exhibited significant activity in delaying seizure generation for all seizure parameters and death as compared to control ($p<0.01$) (FIG. 9B). Regarding the active bisabolene sesquiterpenoids, ar-turmerone and α,β-turmerone were assessed using the mouse PTZ seizure model (FIG. 10). Mice infused with a dose of 50 mg/kg of ar-turmerone exhibited significant resistance to the generation of seizures leading to an increase in the required dose of PTZ to trigger all assessed events: tonic hindlimb extension ($p<0.05$) and ear, myoclonic and tail twitch, forelimb clonus, falling and death ($p<0.01$). Likewise, the anticonvulsant activity of α,β-turmerone was evaluated, and positive results were also found with a dose of 100 mg/kg for all seizure parameters: forelimb clonus, falling, ear and tail twitch ($p<0.05$) and myoclonic twitch, tonic hindlimb extension and death ($p<0.01$). α-Atlantone was not tested in the mouse model since the collected amount was not sufficient to carry out the assay.

Sodium valproate was included as positive control in our PTZ tail infusion method for AED screening in mice (FIG. 11). Using this assay, sodium valproate (50 mg/kg) was capable of delaying tonic hindlimb extension ($p<0.01$) and death ($p<0.05$). Sodium valproate was also able to control seizures generation in zebrafish larvae where it was also used as positive control (FIG. 11).

Example 8

Statistical Analysis

All statistical analyses were performed using GraphPad Prism 5 software (GraphPad Software, Inc.). Values were presented as means±standard deviation (SD). The locomotor activity of zebrafish larvae was analyzed using one-way ANOVA followed by Dunnett's multiple comparison test. Statistically significant differences ($p<0.05$) between a treated group and the equivalent control groups (vehicle or PTZ) were considered indicative of decrease or increase in locomotor activity of zebrafish larvae. For mouse experiments, significant differences between estimated time intervals prior to above-mentioned seizure stages were calculated using the unpaired Student's t-test.

Example 9

Anti-convulsant Activity Evaluation of ar-tumerone in the 6 Hz Psychomotor Seizure Model of Partial Epilepsy For assessing the anti-convulsant activity of ar-Tumerone, the 6 Hz psychomotor seizure model of partial epilepsy (Barton M. E. et al., 2001) was used, thereby applying the following stimulation parameters: 6 Hz, 0.2 ms rectangular pulse width, 3 s duration.

Every mouse (male NMRI+/−30 g) was administered the compound (ar-tumerone 50 mg/kg, 20 mg/kg, 1 mg/kg and 100 µg/kg) or vehicle (PEG 200:DMSO 1:1) via i.p. injection. After 30 minutes of incubation, seizures were induced via corneal stimulation using the Ugo-Basil device. Prior to the placement of corneal electrodes, a drop of 0.5% xylocaine was applied to the eyes of the animal. Animals were restrained manually and released immediately in a transparent plastic cage following the stimulation. Then, the animal was observed. The seizure was characterized by stun, forelimb clonus, twitching of vibrissae, straub-tail for at least 45 s. Protection was defined as the absence of a seizure. A minimum of six animals per dose was used. Six out of six mice showed protection with concentrations of 100 µg/kg, and 1, 20, 50 mg/kg ar-turmerone (FIG. 13). Negative control (only vehicle) and positive control (valproic acid 300 mg/kg) were included as well. As expected, 6 out of 6 mice treated with only vehicle were not protected and 6 out of 6 mice treated with valproic acid were protected.

Example 10

Motor Coordination and Balance on the Elevated Bridge

In this example, the motor coordination and balance of mice using the elevated bridge was observed as described in (Brooks et al., 2012).

The elevated bridge measures the ability of a mouse (male C57B1/6+/−25 g) to traverse the beam without losing its balance (measured as footslips). Every mouse was trained until proficient at running the beam without pausing during the traverse. Two areas of the beam are designated the 'start' and 'stop' areas to allow the operator to start and stop the timing of the animal when running the beam. Following training, every mouse was administered the compound or vehicle via i.v. injection. After 10 minutes, the mouse was placed on the tip of the beam in the star facing towards the beam. The operator timed from the start line until the mouse reaches the stop line. The number of footslips (FIG. 12A), falls (FIG. 12B) and total time (FIG. 12C) on the beam (from 'start' to 'stop' areas) were counted. In this test, 5 out of 5 mice treated with ar-turmerone 50 mg/kg showed a behaviour comparable to the control group (treated with vehicle). Thus, from the obtained results it can be suggested that ar-turmerone does not cause motor or balance impairment as side effect of its anticonvulsant activity. Mice treated with diazepam were included due to the well-know side effect of this AED to cause motor and balance alterations in mice after i.v./i.p. administration.

DISCUSSION

The zebrafish PTZ-induced seizure model (24) was validated using first-line AEDs: phenytoin and diazepam. Additional validation of this screening system was achieved by identification of the known anticonvulsant properties of curcuminoids. Curcumin has often been cited as the main active substance responsible for the anticonvulsant properties of turmeric (11) (12) (32). Although its medicinal properties have been demonstrated, Phase I clinical trials have revealed important pharmacokinetic limitations for curcumin. When administered p.o., the small amount of curcumin absorbed through the gut is mostly converted to water-soluble metabolites and excreted. Thus, the amount of curcumin reaching the circulation is very low. Therefore bioavailability issues have notably limited its therapeutical applications. Thus, several formulation studies have been performed to enhance curcumin bioavailability (33).

On the other hand, neuroprotective studies in rodent models have shown that turmeric oil and its main bisabolene sesquiterpenoids easily cross the blood-brain barrier likely due to their lipophilic nature which allows them to pass through cell membranes (18). Since turmeric oil and its constituents present better bioavailability and cross biomembranes with less difficulty when compared to curcumin (15) (16) (33), our finding that turmeric oil also displays anticonvulsant properties is indeed interesting. Moreover, turmeric safety is supported by the fact that it has been widely used as a food condiment predominantly in India for centuries and its use has been approved for human consumption. Furthermore, toxicity studies performed in human healthy patients (34) and in silico analysis (35) have predicted ar-turmerone as a safe potential candidate for further drug development.

Previous studies on the volatile constituents of turmeric oil were limited due to their complex isolation. Our work presents a practical method to isolate the main constituents of turmeric oil through RP-HPLC. The isolated compounds were individually evaluated in the zebrafish PTZ epilepsy model (data not shown for peaks 1, 3, 8). This model revealed significant activity for turmeric oil and the major bisabolene sesquiterpenoids: ar-; α,β-turmerone (curlone) and α-atlantone. Moreover, the anticonvulsant properties of turmeric oil (50 and 100 mg/kg), ar-turmerone (200 mg/kg), and α-,β-turmerone (100 mg/kg) were successfully corroborated in mice PTZ model and 6 Hz psychomotor seizure model of partial epilepsy. Regarding to the activity of turmeric oil vs ar-turmerone, it seems to be an additive activity since it is necessary higher dose of the isolated bisabolene sesquiterpenoid to observe anticonvusant properties in this model. Nevertheless, these findings reveal the major bisabolene sesquiterpenoids, especially ar-turmerone, as potential anticonvulsant drug candidates to be investigated further.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES

1. World Health Organization. *Atlas: Epilepsy Care in the World*. s.l.: WHO Press, 2005. ISBN 9241563036.
2. *Drug treatment of epilepsy: options and limitations.* Schimdt, D. 2009, Epilepsy and Behavior, Vol. 15, pp. 56-65.
3. *Life-threatening adverse events of antiepileptic drugs.* Arroyo, S. and de la Morena, A. 1-2, 2001, Epilepsy Res, Vol. 47, pp. 155-74.
4. *Complaints associated with the use of antiepileptic drugs: results from a community-based study.* Carpaya, J., Aldenkampb, A. P. and van Donselaa, C. A. 3, 2005, Seizure, Vol. 14, pp. 198-206.
5. *Patient-reported cognitive side effects of antiepileptic drugs: Predictors and comparison of all commonly used antiepileptic drugs.* Arifa, H., et al. 1, 2009, Epilepsy & Behaviour, Vol. 14, pp. 202-9.
6. *Cognitive and memory effects of the new antiepileptic drugs.* Meador, K. 2006, Epilepsy Res, Vol. 68, pp. 63-7.
7. *Review on phytotherapy in epilepsy.* Nsour, W. M., CB-S., Lau and I. C. K., Wong. 2000, Seizure, Vol. 9, pp. 96-107.
8. *New anticonvulsant agents.* Malawska, B. 2005, Current topic in medicinal chemisty, Vol. 5, pp. 69-85.
9. *Losigamone.* Schwabe, W. and Willmore, L. J. 2001, Curr. Op. Invet. Drugs, Vol. 2, pp. 1763-66.
10. *WHO monographs on selected medicinal plants.* World Health Organization. s.l.: WHO Library Cataloguing in Publication Data, 1999, Vol. 1, pp. 115-24. ISBN 924154517 8.
11. *Curcumin protects against electrobehavioral progression of seizures in the iron-induced experimental model of epileptogenesis.* Jyoti, A., Sethi, P. and Sharma, D. 2009, Epilepsy & Behavior, Vol. 14, pp. 300-8.
12. *Protective role of curcumin in maximal electroshock induced seizures, memory impairment and neurotransmit-* ters in rat brain. Jithendra, C., Murthy, T. and Upadyay, L. 1, 2008, Journal of Pre-Clinical and Clinical Res, Vol. 2, pp. 35-9.
13. Prevention of kainic acid-induced changes in nitric oxide level and neuronal cell damage in the rat hippocampus by manganese complexes of curcumin and diacetyl-curcumin. Sumanot, Y., et al. 2006, Life Sci, Vol. 78, pp. 1884-91.
14. Protective effect of curcumin against seizures and cognitive impairment in a pentylenetetrazol-kindled epileptic rat model. Mehla, J., et al. 19-22, 2010, Life Sci, Vol. 87, pp. 596-603.
15. Curcuma oil modulates the nitric oxide system response to cerebral ischemia/reperfusion injury. Dohare, P., Varma, S. and Ray, M. 2008, Nitric Oxide, Vol. 19, pp. 1-11.
16. Neuroprotective efficacy and therapeutic window of curcuma oil: in rat embolic stroke model. Dohare, P., et al. 55, 2008, BCM Complement Altern Med, Vol. 8.
17. Curcuma oil: reduces early accumulation of oxidative product and is anti-apoptogenic in transient focal ischemia in rat brain. Rathore, P., et al. 2008, Neurochem Res, Vol. 33, pp. 1672-82.
18. Anticonvulsant activity of furanocoumarins and the essential oil obtained from the fruits of Heracleum crenatifolium. Tosun, F., et al. 3, 2008, Food Chemistry, Vol. 107, pp. 990-3.
19. Phytochemical screening and anticonvulsant activity of Cymbopogon winterianus Jowitt (Poacea) leaf essential oil in rodents. Quintans-Júnior, L. J., et al. 8, 2008, Phytomedicine, Vol. 15, pp. 619-24.
20. Anticonvulsant activity of the leaf essential oil of Laurus nobilis against pentylenetetrazole-and maximal electroshock-induced seizures. Sayyah, M., Valizadeh, J. and Kamalinejad, M. 3, 2002, Phytomedicine, Vol. 9, pp. 212-6.
21. Acute effects of alcohol on larval zebrafish: a genetic system for large-scale screening. Lockwood, B., et al. 2009, Pharmacology, Biochemistry and Behavior, Vol. 77, pp. 647-54.
22. In vivo drug discovery in the zebrafish. Zon, L. and Peterson, R. 2005, Nature Reviews Drug Discovery, Vol. 4, pp. 35-44.
23. Pentylenetetrazole-induced changes in zebrafish behavior, neural activity, and c-fos expression. Baraban, S. C., Taylor, M. R.: Castro, P. A. and Baier, H. 3, 2005, Neuroscience, Vol. 131, pp. 759-68.
24. Zebrafish offer the potential for a primary screen to identify a wide variety of potential anticonvulsants. Berghmans, S., et al. 1, 2007, Epilepsy Res, Vol. 75, pp. 18-28.
25. Validation of a larval zebrafish locomotor assay for assessing the seizure liability of early-stage development drugs. Winter, M. J., et al. 2008, Journal of Pharmacological and Toxicological Methods, Vol. 57, pp. 178-87.
26. Jackson, B. P. Atlas of microscopy of medicinal plants, culinary herbs and spices. London, UK: CRC Press, 1990. ISBN 0849377056.
27. Liquid chromatography-electrospray mass spectrometric analysis of curcuminoids and sesquiterpenoids in turmeric (Curcuma longa). He, X-G., et al. 1998, Journal of Chromatography A, Vol. 818, pp. 127-32.
28. Acute seizure tests in epilepsy research: electroshock- and chemical-induced convulsions in the mice. Giardina, W. J. and Gasior, M. 5.22.27, 2009, Curr. Protoc. Pharmacol, Vol. 45.
29. Total synthesis of (R)- and (S)-turmerone and (7S,9R)-bisacumol by an efficient chemoenzymatic approach. Kamal, A., et al. 11, 2009, Tetrahedron: Asymmetry, Vol. 20, pp. 1267-71.
30. New bisabolane sesquiterpenoids from the rhizomes of Curcuma xanthorrhiza (Zingiberacea). Uehara, S., et al. 1989, Chem Pharm Bull, Vol. 37, pp. 237-40.
31. Preparation of $\gamma,\delta$-unsaturated $\beta$-ketophosphonates from tertiary $\alpha$-allenic alcohols. The Synthesis of ($\pm$)-(E)-$\alpha$-Atlantone. Friesen, R. W. and Blouin, M. 1996, J. Org. Chem, Vol. 61, pp. 7202-6.
32. Curcumin has anticonvulsant activity on increasing current electroshock seizures in mice. Bharal, N., et al. 2008, Phytotherapy Res, Vol. 22, pp. 1660-4.
33. A pilot cross-over study to evaluate human oral bioavailability of BCM-95 CG (Biocurcumax), a novel bioenhanced preparation of curcumin. Antony, B., et al. 4, 2008, Indian J Pharm Sci, Vol. 70, pp. 445-9.
34. Early human safety study of turmeric oil (Curcuma longa oil) administered orally in healthy volunteers. Joshi, J., et al. 2003, JAPI, Vol. 51.
35. Toxicity prediction of compounds from turmeric (Curcuma longa L.). Balaji, S. and Chempakam, B. 2010, Food Chem Toxicol, Vol. 48, pp. 2951-9.
36. $\alpha$-Tocopherol protects against pentylenetetrazol-and methylmalonate-induced convulsions. Pereira, M., et al. 1, 2005, Epilepsy Res, Vol. 66, pp. 185-94.
37. Regional vulnerability to oxidative stress in a model of experimental epilepsy. Lores Arnaiz, S., et al. 12, Neurochemical Res, Vol. 23, pp. 1477-83.
38. Protective effect of curcumin against seizures and cognitive impairment in a pentylenetetrazol-kindled epileptic rat model. Mehla J, Reeta K. H, Gupta P, Gupta Y. s.l.: Life Sci, 2010, Vols. 87, Issues 19-22, pp. 596-603.
39. El Jazouli M, Lage N, Masson S, Thuillier A. s.l.: Bull Soc Chim Fr, 1988, Vol. 5, pp. 883-8.
40. Pharmacological characterization of the 6 Hz psychomotor seizure model of partial epilepsy. Barton M E, Klein B D, Wolf H H, White H S. Epilepsy Res. 2001 December; 47(3):217-27.
41. Acetylcholinesterase Inhibitory Activity of Volatile Oil from Peltophorum dasyrachis Kurz ex Bakar (Yellow Batai) and Bisabolane-Type Sesquiterpenoids. Fujiwara M, Yagi N, Miyazawa M. J. Agric Food Chem. 2010, 58: 2824-2829
42. Cholinergic Dysfunction in Temporal Lobe Epilepsy. Friedman A, Beherens C, Heinemann U. Epilepsia 2007, 48 (Suppl5): 126-130.

The invention claimed is:

1. A method for treating convulsive disorders of the central nervous system comprising administering to a subject in need thereof an effective amount of an anticonvulsant therapeutic agent consisting of one or more bisabolene sesquiterpenoids of turmeric essential oil.

2. The method of claim 1 wherein the turmeric essential oil is obtained from a *Curcuma* genus.

3. The method of claim 1 wherein the one or more bisabolene sesquiterpenoids is selected from the group consisting of Ar-turmerone, $\alpha$-turmerone, $\beta$-turmerone, and $\alpha$-atlantone, and combinations thereof.

4. The method of claim 1 wherein the anticonvulsant therapeutic agent is in the form of a liquid composition.

5. The method of claim 1 wherein the convulsive disorders of the central nervous system include epileptic seizures, symptoms associated with epileptic seizures, seizure-like behaviors, epilepsy, and tremor.

6. The method of claim 1 wherein the convulsive disorder of the central nervous system is epilepsy.

7. A method for treating convulsive disorders of the central nervous system comprising administering to a subject in need thereof an effective amount of an anticonvulsant therapeutic agent consisting of turmeric essential oil.

8. The method of claim 7 wherein the convulsive disorders of the central nervous system include epileptic seizures, symptoms associated with epileptic seizures, seizure-like behaviors, epilepsy, and tremor.

9. The method of claim 7 wherein the convulsive disorder of the central nervous system is epilepsy.

* * * * *